United States Patent
Hayashi

(10) Patent No.: US 11,503,980 B2
(45) Date of Patent: Nov. 22, 2022

(54) SURGICAL SYSTEM AND SURGICAL IMAGING DEVICE

(71) Applicant: SONY CORPORATION, Tokyo (JP)

(72) Inventor: Tsuneo Hayashi, Tokyo (JP)

(73) Assignee: SONY CORPORATION, Tokyo (JP)

(*) Notice: Subject to any disclaimer, the term of this patent is extended or adjusted under 35 U.S.C. 154(b) by 192 days.

(21) Appl. No.: 16/621,888

(22) PCT Filed: Jun. 7, 2018

(86) PCT No.: PCT/JP2018/021808
§ 371 (c)(1),
(2) Date: Dec. 12, 2019

(87) PCT Pub. No.: WO2018/235608
PCT Pub. Date: Dec. 27, 2018

(65) Prior Publication Data
US 2020/0113413 A1 Apr. 16, 2020

(30) Foreign Application Priority Data
Jun. 21, 2017 (JP) .............................. JP2017-121132

(51) Int. Cl.
*A61B 1/00* (2006.01)

(52) U.S. Cl.
CPC ...... *A61B 1/00009* (2013.01); *A61B 1/00006* (2013.01); *A61B 1/00045* (2013.01); *A61B 1/00172* (2013.01); *A61B 1/00188* (2013.01)

(58) Field of Classification Search
CPC ............ A61B 1/00009; A61B 1/00006; A61B 1/00045; A61B 1/00172; A61B 1/00188
See application file for complete search history.

(56) References Cited

U.S. PATENT DOCUMENTS

2002/0147384 A1 10/2002 Uchikubo
2004/0210105 A1* 10/2004 Hale .................. A61B 1/00009
600/101
(Continued)

FOREIGN PATENT DOCUMENTS

JP  2011-211553 A  10/2011
JP  2012-137665 A  7/2012
(Continued)

OTHER PUBLICATIONS

International Search Report and Written Opinion of PCT Application No. PCT/JP2018/021808, dated Aug. 21, 2018, 09 pages of ISRWO.
(Continued)

*Primary Examiner* — Timothy J Neal
*Assistant Examiner* — William B Chou
(74) *Attorney, Agent, or Firm* — Chip Law Group

(57) ABSTRACT

The present technology relates to a surgical system and a surgical imaging device enabled to reduce latency. The surgical imaging device generates a surgical image by imaging the inside of a living body, a signal processing device performs predetermined signal processing on the surgical image, and a display device displays the surgical image on which the signal processing is performed. The imaging device generates the surgical image on the basis of scan information indicating a scan order of the surgical image. The present technology can be applied to, for example, an endoscopic surgical system.

13 Claims, 23 Drawing Sheets

(56) References Cited

U.S. PATENT DOCUMENTS

| | | | | |
|---|---|---|---|---|
| 2008/0159653 A1* | 7/2008 | Dunki-Jacobs | ......... | A61B 1/04 |
| | | | | 382/293 |
| 2013/0342667 A1* | 12/2013 | Miyayashiki | ........ | A61B 1/0005 |
| | | | | 348/65 |
| 2016/0174822 A1 | 6/2016 | Stith et al. | | |
| 2018/0027165 A1 | 1/2018 | Murakita | | |

FOREIGN PATENT DOCUMENTS

| | | |
|---|---|---|
| JP | 2013-162874 A | 8/2013 |
| JP | 2014-200547 A | 10/2014 |
| WO | 2011/040769 A2 | 4/2011 |
| WO | 2016/100731 A1 | 6/2016 |
| WO | 2016/129162 A1 | 8/2016 |
| WO | 2017/038241 A1 | 3/2017 |

OTHER PUBLICATIONS

Office Action for CN Patent Application No. 201880038931.7, dated Dec. 24, 2021, 11 pages of English Translation and 08 pages of Office Action.

* cited by examiner

FIG. 16

| INVERSION SPECIFICATION OF TOP AND BOTTOM DIRECTION OF DISPLAY DEVICE 203-1 | INVERSION SPECIFICATION OF TOP AND BOTTOM DIRECTION OF DISPLAY DEVICE 203-2 | SCAN ORDER OF IMAGING DEVICE 201 | LATENCY OF DISPLAY DEVICE 203-1 | LATENCY OF DISPLAY DEVICE 203-2 |
|---|---|---|---|---|
| NO | NO | FORWARD DIRECTION | 0V | 0V |
| NO | YES | FORWARD DIRECTION | 0V OR 1V | 1V |
| YES | NO | FORWARD DIRECTION | 1V | 0V OR 1V |
| YES | YES | BACKWARD DIRECTION | 0V | 0V |

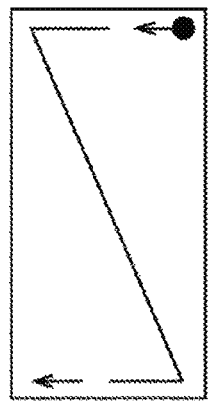
FIG. 22B
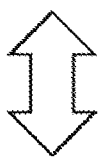
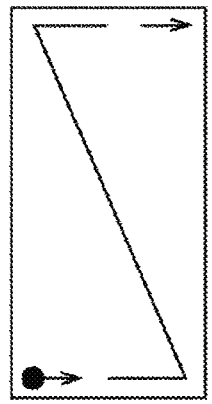
FIG. 22A

SURGICAL SYSTEM AND SURGICAL IMAGING DEVICE

CROSS REFERENCE TO RELATED APPLICATIONS

This application is a U.S. National Phase of International Patent Application No. PCT/JP2018/021808 filed on Jun. 7, 2018, which claims priority benefit of Japanese Patent Application No. JP 2017-121132 filed in the Japan Patent Office on Jun. 21, 2017. Each of the above-referenced applications is hereby incorporated herein by reference in its entirety.

TECHNICAL FIELD

The present technology relates to a surgical system and a surgical imaging device, and more particularly, to a surgical system and a surgical imaging device enabled to reduce latency.

BACKGROUND ART

In endoscopic surgery, there has conventionally been a case where a direction of the top and bottom of an image to be displayed on a display device is opposite to a direction of the top and bottom determined by the direction of gravity, depending on a direction of the top and bottom of an endoscope inserted into an abdominal cavity. In such a case, an image inversion function is provided in the display device, whereby the image has been inverted and displayed.

For example, Patent Document 1 discloses an endoscopic surgical system that displays an image for each of a main surgeon and a sub-surgeon in a display direction depending on a standing position of each of the main surgeon and the sub-surgeon.

Transmission of the image from the endoscope to the display device is performed serially such as raster scan. Therefore, to invert and display the image on the display device, it has been necessary to store one image in a memory in the display device.

CITATION LIST

Patent Document

Patent Document 1: Japanese Patent Application Laid-Open No. 2014-200547

SUMMARY OF THE INVENTION

Problems to be Solved by the Invention

Thus, in a case where the image inversion function is provided in the display device, it has been necessary for the display device to wait for completion of storage of one image in the memory and then perform scanning for display. In other words, a delay (latency) has occurred of a transmission time for one screen.

The present technology has been made in view of such a situation, and it is intended to reduce the latency.

Solutions to Problems

A surgical system of the present technology includes: a surgical imaging device that generates a surgical image by imaging the inside of a living body; a signal processing device that performs predetermined signal processing on the surgical image; and a display device that displays the surgical image on which the signal processing is performed, in which the surgical imaging device generates the surgical image on the basis of scan information indicating a scan order of the surgical image.

The signal processing device can be caused to perform the signal processing on the surgical image on the basis of the scan information, and the display device can be caused to display the surgical image on the basis of the scan information.

A scan information generation unit can be further provided that generates the scan information depending on a top and bottom direction of the surgical image to be displayed on the display device.

The display device can be provided with: a user interface that accepts specification of the top and bottom direction of the surgical image to be displayed on the display device; and the scan information generation unit, and the scan information generation unit can be caused to generate the scan information on the basis of the specification of the top and bottom direction of the surgical image accepted by the user interface.

The signal processing device can be provided with: a user interface that accepts specification of the top and bottom direction of the surgical image to be displayed on the display device; and the scan information generation unit, and the scan information generation unit can be caused to generate the scan information on the basis of the specification of the top and bottom direction of the surgical image accepted by the user interface.

The surgical imaging device can be provided with: a user interface that accepts specification of the top and bottom direction of the surgical image to be displayed on the display device; and the scan information generation unit, and the scan information generation unit can be caused to generate the scan information on the basis of the specification of the top and bottom direction of the surgical image accepted by the user interface.

A controller can be further provided that controls each device constituting the surgical system is further provided, and the controller can be provided with: a user interface that accepts specification of the top and bottom direction of the surgical image to be displayed on the display device; and the scan information generation unit, and the scan information generation unit can be caused to generate the scan information on the basis of the specification of the top and bottom direction of the surgical image accepted by the user interface.

A plurality of the display devices can be provided, and the user interface can be caused to accept specification of the top and bottom direction of the surgical image displayed on each of the plurality of display devices.

A scan information generation unit can be further provided that generates the scan information on the basis of a positional relationship among a user, the surgical imaging device, and the display device.

A detection device can be further provided that generates top and bottom information indicating a direction of the top and bottom of the surgical imaging device on the basis of the direction of gravity detected in the surgical imaging device, and the scan information generation unit can be further provided that generates the scan information on the basis of the top and bottom information.

A surgical imaging device of the present technology includes an imaging unit that generates a surgical image by imaging the inside of a living body, in which the imaging unit generates the surgical image on the basis of scan information indicating a scan order of the surgical image corresponding to the top and bottom direction of the surgical image to be displayed on a display device.

In the present technology, the surgical image is generated on the basis of the scan information indicating the scan order of the surgical image.

Effects of the Invention

According to the present technology, the latency can be reduced. Note that, the effect described here is not necessarily limited, and can be any effect described in the present disclosure.

BRIEF DESCRIPTION OF DRAWINGS

FIG. 16 is a diagram for explaining a relationship between a scan order of an imaging device and latency.

FIGS. 22A and 22B are diagrams illustrating an example of another scan order.

MODE FOR CARRYING OUT THE INVENTION

Figure 1:
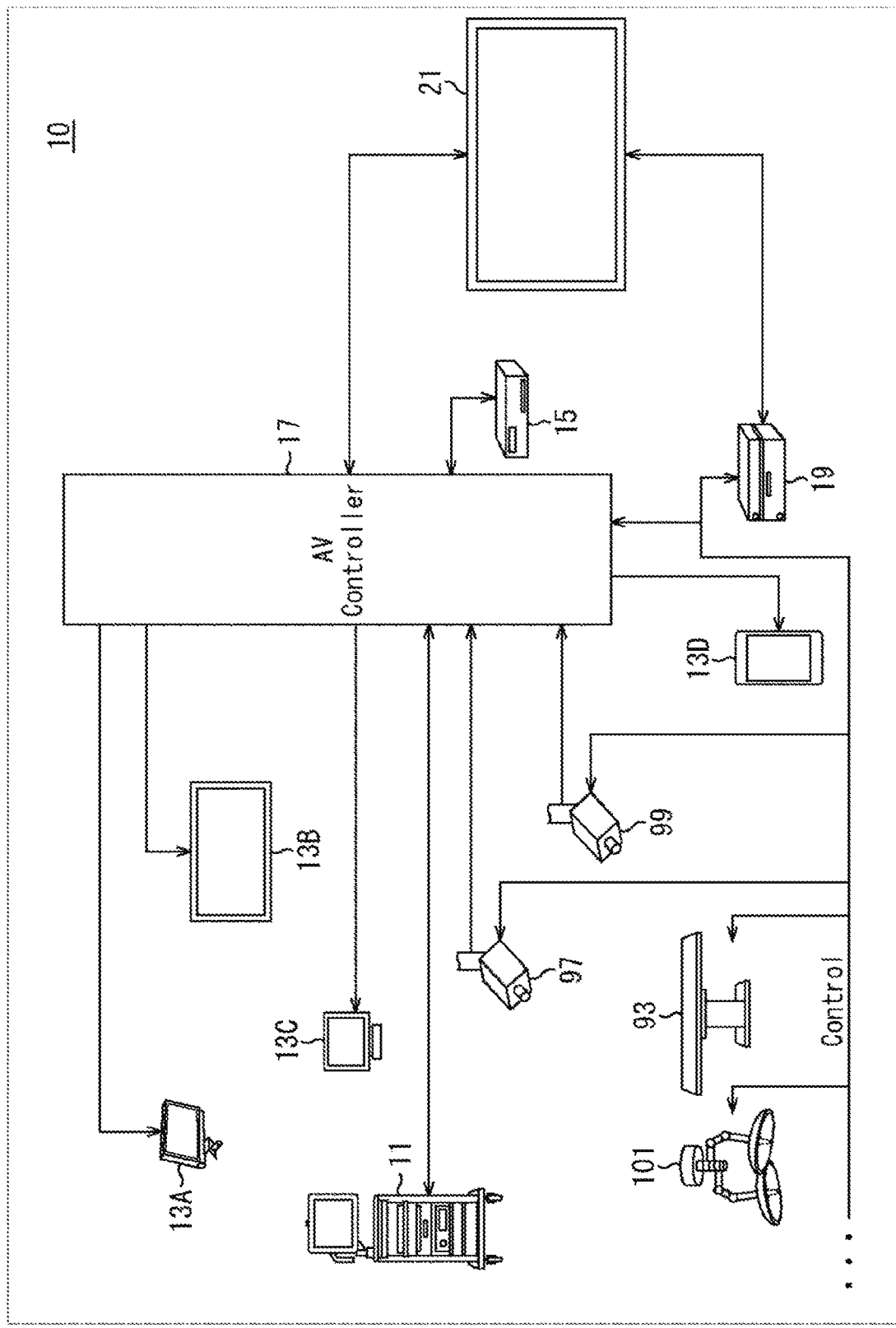
FIG. 1 is a diagram schematically illustrating an overall configuration of an operation room system.

The following is a description of a mode for carrying out the present disclosure (the mode will be hereinafter referred to as the embodiment). Note that, description will be made in the following order.

1. Outline of operation room system
2. Endoscopic surgical system to which the present technology is applied
3. First modification
4. Second modification
5. Third modification
6. Fourth modification
7. Fifth modification
8. Sixth modification
9. Seventh modification
10. Eighth modification
11. Endoscopic surgical systems of other embodiments
12. Others 1. Outline of Operation Room System First, an outline will be described of an operation room system to which the present technology is applied.

FIG. 1 is a diagram schematically illustrating an overall configuration of an operation room system 10 to which a technology according to the present disclosure can be applied.

As illustrated in FIG. 1, the operation room system 10 includes devices installed in an operation room, the devices being connected to each other to be able to cooperate with each other via an audiovisual controller (AV controller) 17 and an operation room control device 19.

Various devices can be installed in the operation room. The example of FIG. 1 illustrates various devices 11 for endoscopic surgery, a ceiling camera 97 that is provided on the ceiling of the operation room and images an area at hand of a surgeon, an operation room camera 99 that is provided on the ceiling of the operation room and images a state of the entire operation room, a plurality of display devices 13A to 13D, a recorder 15, a patient bed 93, and an illumination 101.

Here, among these devices, the devices 11 belongs to an endoscopic surgical system 23 as described later, and includes an endoscope, a display device that displays an image captured by the endoscope, and the like. Each device that belongs to the endoscopic surgical system 23 is also called a medical device. On the other hand, the display devices 13A to 13D, the recorder 15, the patient bed 93, and the illumination 101 are devices provided in, for example, the operation room, separately from the endoscopic surgical system 23. Each device that does not belong to the endoscopic surgical system 23 is also called a non-medical device. The audiovisual controller 17 and/or the operation room control device 19 controls operations of these medical devices and non-medical devices in cooperation with each other.

The audiovisual controller 17 comprehensively controls processing regarding image display in the medical devices and non-medical devices. Specifically, among the devices included in the operation room system 10, the devices 11, the ceiling camera 97, and the operation room camera 99 each are a device (hereinafter also referred to as a transmission source device) having a function of transmitting information (hereinafter also referred to as display information) to be displayed during surgery. Furthermore, the display devices 13A to 13D each are a device (hereinafter also referred to as an output destination device) that outputs the display information. Moreover, the recorder 15 is a device corresponding to both the transmission source device and the output destination device. The audiovisual controller 17 has functions of controlling operations of the transmission source device and the output destination device, to acquire the display information from the transmission source device and transmit the display information to the output destination device for display or recording. Note that, the display information is various images captured during the surgery, and various types of information regarding the surgery (for example, patient's physical information, the past examination results, information about a surgical method, and the like).

The audiovisual controller 17 causes at least one of the display devices 13A to 13D that are output destination devices to display the acquired display information (in other words, images captured during the surgery, and various types of information regarding the surgery). In the example of FIG. 1, the display device 13A is a display device suspended from the ceiling of the operation room, and the display device 13B is a display device installed on a wall surface of the operation room. Furthermore, the display device 13C is a display device installed on a desk in the operation room, and the display device 13D is a mobile device (for example, a tablet personal computer (PC)) having a display function.

Furthermore, although illustration is omitted in FIG. 1, the operation room system 10 may include devices outside the operation room. The devices outside the operation room are, for example, a server connected to a network built inside and outside a hospital, a PC used by a medical staff, a projector installed in a conference room of the hospital, and the like. In a case where such an external device is outside the hospital, the audiovisual controller 17 can also cause a display device of another hospital to display the display information via a video conference system or the like, for telemedicine.

The operation room control device 19 comprehensively controls processing other than the processing regarding the image display in the non-medical devices. For example, the operation room control device 19 controls drive of the patient bed 93, the ceiling camera 97, the operation room camera 99, and the illumination 101.

The operation room system 10 is provided with a centralized operation panel 21. A user can give an instruction about image display to the audiovisual controller 17 via the centralized operation panel 21, or an instruction about operation of the non-medical device to the operation room control device 19. The centralized operation panel 21 is configured as a touch panel provided on the display surface of the display device.

Figure 2:
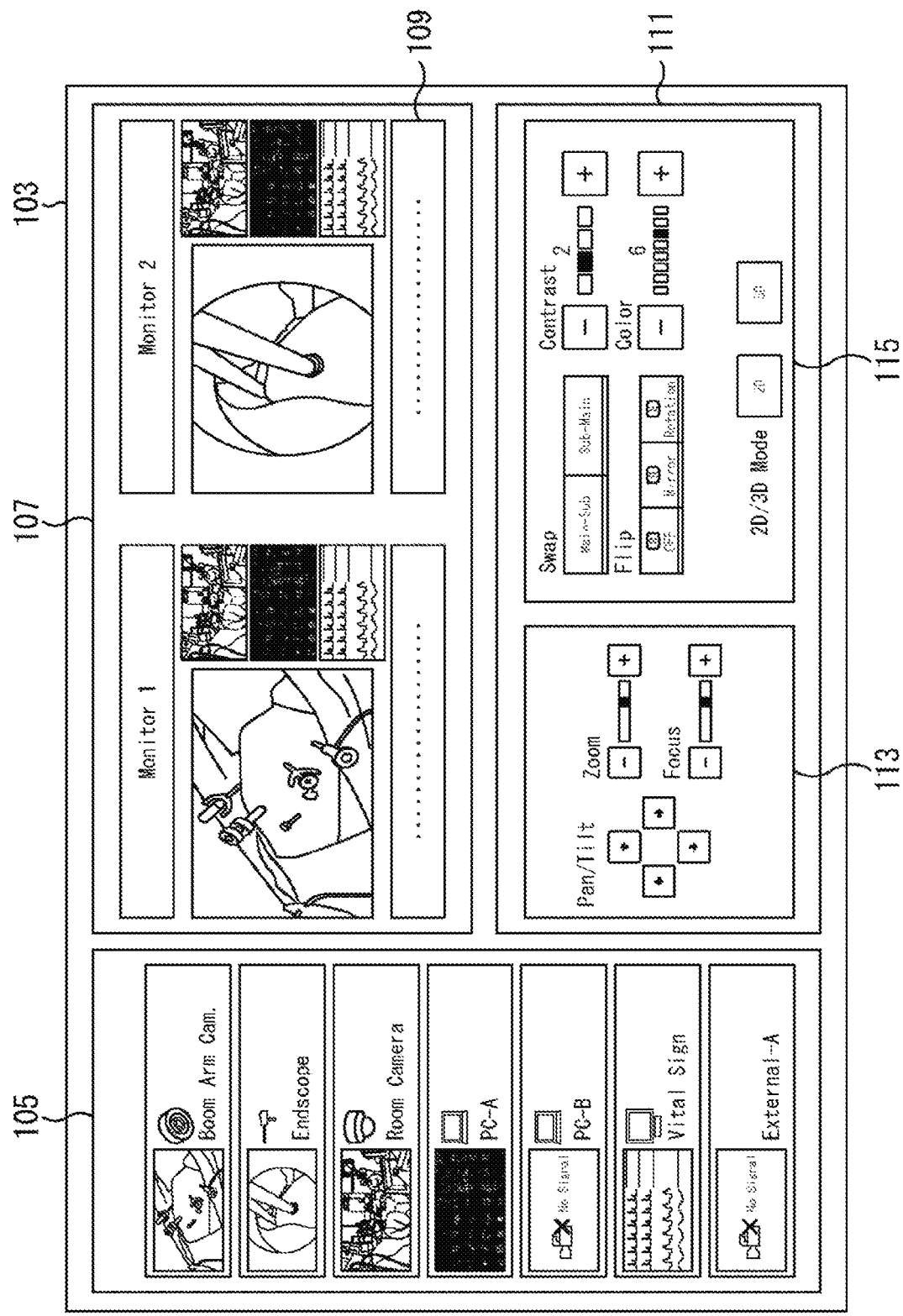
FIG. 2 is a diagram illustrating a display example of an operation screen on a centralized operation panel.

FIG. 2 is a diagram illustrating a display example of an operation screen on the centralized operation panel 21.

In the example of FIG. 2, the operation screen is illustrated corresponding to a case where the operation room system 10 is provided with two display devices. An operation screen 103 is provided with a transmission source selection area 105, a preview area 107, and a control area 111.

In the transmission source selection area 105, the transmission source devices included in the operation room system 10 and respective thumbnail screens representing the display information of the transmission source devices are displayed in association with each other. The user can select the display information to be displayed on the display device from any of the transmission source devices displayed in the transmission source selection area 105.

In the preview area 107, previews are displayed of screens displayed on the respective two display devices (Monitor 1 and Monitor 2) that are output destination devices. In the example of FIG. 2, four images are PinP-displayed in one display device. The four images correspond to the display information transmitted from the transmission source device selected in the transmission source selection area 105. Among the four images, one is displayed relatively large as a main image, and the remaining three are displayed relatively small as sub-images. The user can switch the main image and the sub-images with each other by appropriately selecting one of four areas in which the respective images are displayed. Furthermore, a status display area 109 is provided below an area in which the four images are displayed, and a status regarding the surgery (for example, an elapsed time of the surgery, the patient's physical information, and the like) is displayed as appropriate.

The control area 111 is provided with a transmission source operation area 113 in which graphical user interface (GUI) components are displayed for performing operation to the transmission source device, and an output destination operation area 115 in which GUI components are displayed for performing operation to the output destination device to which the display information is output.

In the transmission source operation area 113, the GUI components are provided for performing various operations (pan, tilt, and zoom) to a camera in the transmission source device having an imaging function. The user can operate the operation of the camera in the transmission source device by appropriately selecting these GUI components.

Furthermore, in the output destination operation area 115, the GUI components are provided for performing various operations (swap, flip, color adjustment, contrast adjustment, switching between 2D display and 3D display) to a display on the display device that is the output destination device. The user can operate the display on the display device by appropriately selecting these GUI components.

Note that, the operation screen displayed on the centralized operation panel 21 is not limited to the example of FIG. 2, and the user may be capable of operation input to each device controlled by the audiovisual controller 17 and the operation room control device 19 included in the operation room system 10 via the centralized operation panel 21.

Figure 3:
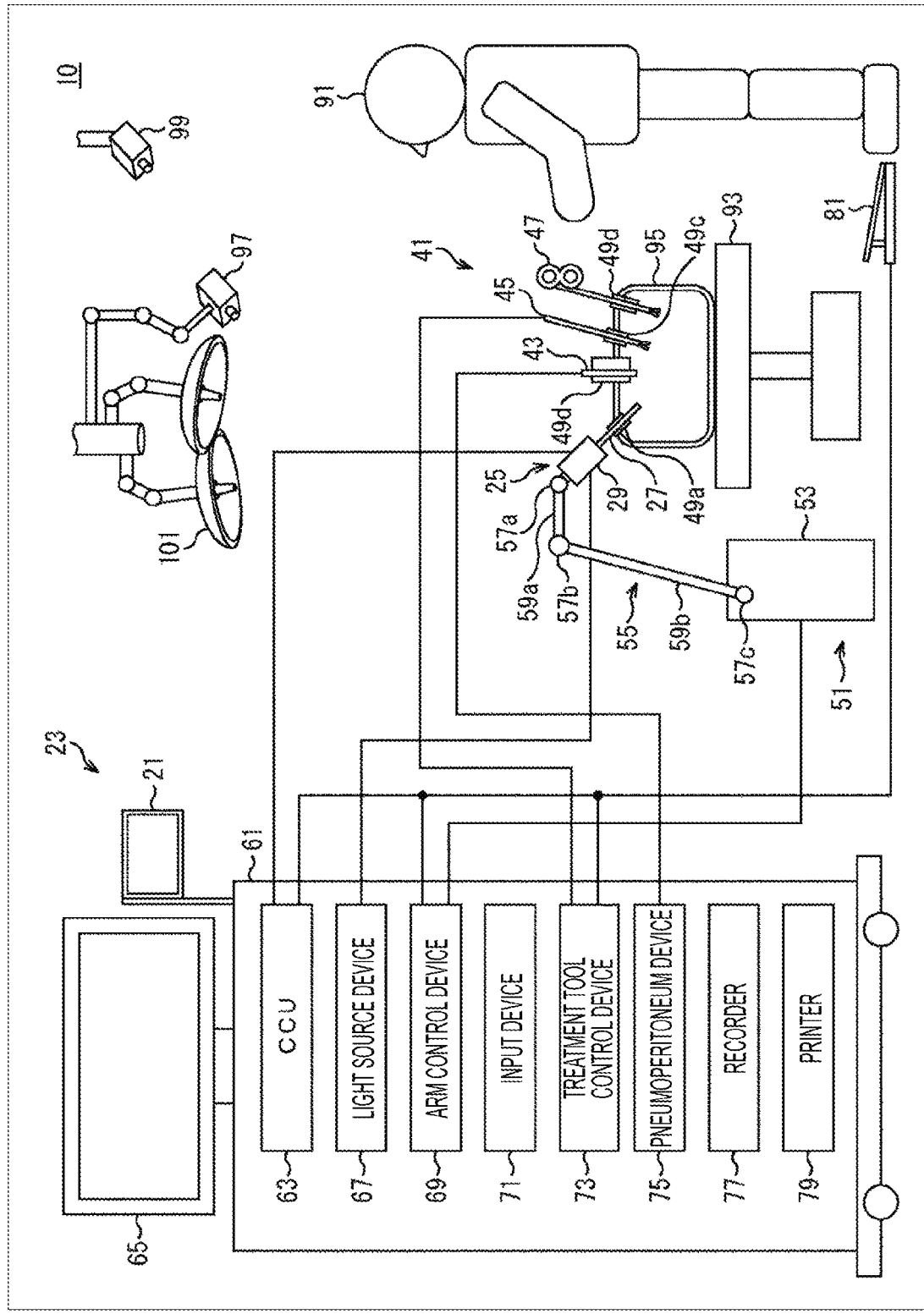
FIG. 3 is a diagram illustrating an example of a state of surgery to which the operation room system is applied.

FIG. 3 is a diagram illustrating an example of a state of the surgery to which the operation room system 10 described above is applied.

The ceiling camera 97 and the operation room camera 99 are provided on the ceiling of the operation room, and can image the state of the area at hand of a surgeon (doctor) 91 who performs treatment on an affected part of a patient 5185 on the patient bed 93, and the entire operation room. The ceiling camera 97 and the operation room camera 99 are provided with a magnification adjustment function, a focal length adjustment function, an imaging direction adjustment function, and the like. The illumination 101 is provided on the ceiling of the operation room, and irradiates at least the area at hand of the surgeon 91. The illumination 101 is enabled to appropriately adjust the amount of irradiation light, the wavelength (color) of the irradiation light, the irradiation direction of the light, and the like.

As described above, the endoscopic surgical system 23, the patient bed 93, the ceiling camera 97, the operation room camera 99, and the illumination 101 are connected to each other to be able to cooperate with each other via the audiovisual controller 17 and the operation room control device 19. The centralized operation panel 21 is provided in the operation room, and as described above, the user can appropriately operate these devices existing in the operation room via the centralized operation panel 21.

The endoscopic surgical system 23 includes an endoscope 25, other surgical tools 41, a support arm device 51 that supports the endoscope 25, and a cart 61 on which various devices are mounted for endoscopic surgery.

In endoscopic surgery, instead of performing laparotomy by incising an abdominal wall, a plurality of cylindrical opening devices called trocars 49a to 49d punctures the abdominal wall. Then, a lens barrel 27 of the endoscope 25 and the other surgical tools 41 are inserted into a body cavity of the patient 95 from the trocars 49a to 49d. In the example of FIG. 3, a pneumoperitoneum tube 43, an energy treatment tool 45, and forceps 47 are inserted into the body cavity of the patient 95 as the other surgical tools 41. The energy treatment tool 45 is a treatment tool that performs incision and peeling of tissue, sealing of a blood vessel, or the like by a high-frequency current or ultrasonic vibration. However, the surgical tools 41 illustrated are merely examples, and various surgical tools generally used in endoscopic surgery may be used as the surgical tools 41, for example, tweezers, a retractor, and the like.

An image of a surgical portion in the body cavity of the patient 95 imaged by the endoscope 25 is displayed on a display device 65. The surgeon 91 performs a treatment, for example, excising the affected part, or the like, by using the energy treatment tool 45 and the forceps 47 while viewing the image of the surgical portion displayed on the display device 65 in real time. Note that, although not illustrated, the pneumoperitoneum tube 43, the energy treatment tool 45, and the forceps 47 are supported by the surgeon 91, an assistant, or the like during the surgery.

The support arm device 51 includes an arm 55 extending from a base 53. In the example of FIG. 3, the arm 55 includes joints 57a, 57b, and 57c and links 59a and 59b, and is driven by control of an arm control device 69. The endoscope 25 is supported by the arm 55, and its position and posture are controlled. As a result, stable position fixing can be implemented of the endoscope 25.

The endoscope 25 includes the lens barrel 27 in which an area of a predetermined length from the distal end is inserted into the body cavity of the patient 95, and a camera head 29 connected to the proximal end of the lens barrel 27. In the example of FIG. 3, the endoscope 25 configured as a so-called rigid scope including a rigid lens barrel 27 is illustrated, but the endoscope 25 may be configured as a so-called flexible scope including a flexible lens barrel 27.

At the distal end of the lens barrel 27, an opening is provided into which an objective lens is fitted. A light source device 67 is connected to the endoscope 25, and light generated by the light source device 67 is guided to the distal end of the lens barrel by a light guide extending inside the lens barrel 27, and the light is emitted toward an observation target in the body cavity of the patient 95 via the objective lens. Note that, the endoscope 25 may be a forward-viewing endoscope, or may be an oblique-viewing endoscope, or a side-viewing endoscope.

An optical system and an imaging element are provided inside the camera head 29, and reflected light (observation light) from the observation target is focused on the imaging element by the optical system. The observation light is photoelectrically converted by the imaging element, and an electric signal corresponding to the observation light, that is, an image signal corresponding to the observation image is generated. The image signal is transmitted as RAW data to a camera control unit (CCU) 63. Note that, in the camera head 29, a function is installed of adjusting the magnification and the focal length by appropriately driving the optical system.

Note that, for example, to cope with stereoscopic vision (3D display) or the like, the camera head 29 may be provided with a plurality of the imaging elements. In this case, a plurality of relay optical systems is provided inside the lens barrel 27 to guide the observation light to each of the plurality of imaging elements.

Various devices are mounted on the cart 137.

The CCU 63 includes a central processing unit (CPU), a graphics processing unit (GPU), and the like, and comprehensively controls operation of the endoscope 25 and the display device 65. Specifically, the CCU 63 performs, on the image signal received from the camera head 29, various types of image processing for displaying an image based on the image signal, for example, development processing (demosaic processing), and the like. The CCU 63 provides the display device 65 with the image signal on which the image processing is performed. Furthermore, the audiovisual controller 17 of FIG. 1 is connected to the CCU 63. The CCU 63 also provides the audiovisual controller 17 with the image signal on which the image processing is performed. Moreover, the CCU 63 transmits a control signal to the camera head 29 to control its drive. The control signal can include information regarding imaging conditions such as the magnification and the focal length. The information regarding the imaging conditions may be input via an input device 71, or may be input via the centralized operation panel 21 described above.

The display device 65 displays the image based on the image signal on which the image processing is performed by the CCU 63, by the control of the CCU 63. In a case where the endoscope 25 is compatible with high-resolution imaging, for example, 4K (the number of horizontal pixels 3840×the number of vertical pixels 2160), 8K (the number of horizontal pixels 7680×the number of vertical pixels 4320), and the like, and/or in a case where the endoscope 25 is compatible with 3D display, as the display device 65, corresponding to each case, a display device is used capable of high-resolution display and/or 3D display. In a case where the display device 65 is compatible with the high-resolution imaging such as 4K or 8K, a more immersive feeling can be obtained by using a display device having a size of greater than or equal to 55 inches. Furthermore, a plurality of the display devices 65 having different resolutions and sizes may be provided depending on applications.

The light source device 67 includes a light source, for example, a light emitting diode (LED) or the like, and supplies irradiation light for imaging the surgical portion to the endoscope 25.

The arm control device 69 includes a processor, for example, a CPU or the like, and controls drive of the arm 55 of the support arm device 51 in accordance with a predetermined control method by operating in accordance with a predetermined program.

The input device 71 is an input interface to the endoscopic surgical system 23. The user can input various types of information and instructions to the endoscopic surgical system 23 via the input device 71. For example, the user inputs various types of information regarding the surgery, such as the patient's physical information and information about the surgical method, via the input device 71. Furthermore, for example, the user inputs, via the input device 71, an instruction to drive the arm 55, an instruction to change the imaging conditions (type of irradiation light, magnification, focal length, and the like) by the endoscope 25, an instruction to drive the energy treatment tool 45, and the like.

The type of the input device 71 is not limited, and the input device 71 may be any of various known input devices. As the input device 71, for example, a mouse, a keyboard, a touch panel, a switch, a foot switch 81 and/or a lever and the like can be applied. In a case where a touch panel is used as the input device 71, the touch panel may be provided on the display surface of the display device 65.

Furthermore, the input device 71 may be a device worn by the user, for example, a glasses-type wearable device, a head mounted display (HMD), or the like. In this case, various inputs are performed depending on the user's gesture and line-of-sight detected by these devices. Furthermore, the input device 71 may include a camera enabled to detect the user's movement, and various inputs may be performed depending on the user's gesture and line-of-sight detected from a video captured by the camera. Moreover, the input device 71 may include a microphone enabled to pick up a user's voice, and various inputs may be performed by voice via the microphone.

As described above, the input device 71 is enabled to input various information without contact, whereby in particular the user (for example, the surgeon 91) belonging to a clean area can operate a device belonging to an unclean area without contact. Furthermore, since the user can operate the device without releasing the user's hand from the surgical tool, convenience of the user is improved.

A treatment tool control device 73 controls drive of the energy treatment tool 45 for cauterization of tissue, incision, sealing of blood vessels, or the like. A pneumoperitoneum device 75 injects a gas into the body cavity via the pneumoperitoneum tube 43 to inflate the body cavity of the patient 95, for the purpose of securing a visual field by the endoscope 25 and securing a working space of the surgeon. A recorder 77 is a device enabled to record various types of information regarding the surgery. A printer 79 is a device enabled to print various types of information regarding the surgery in various formats such as text, image, graph, and the like.

Figure 4:
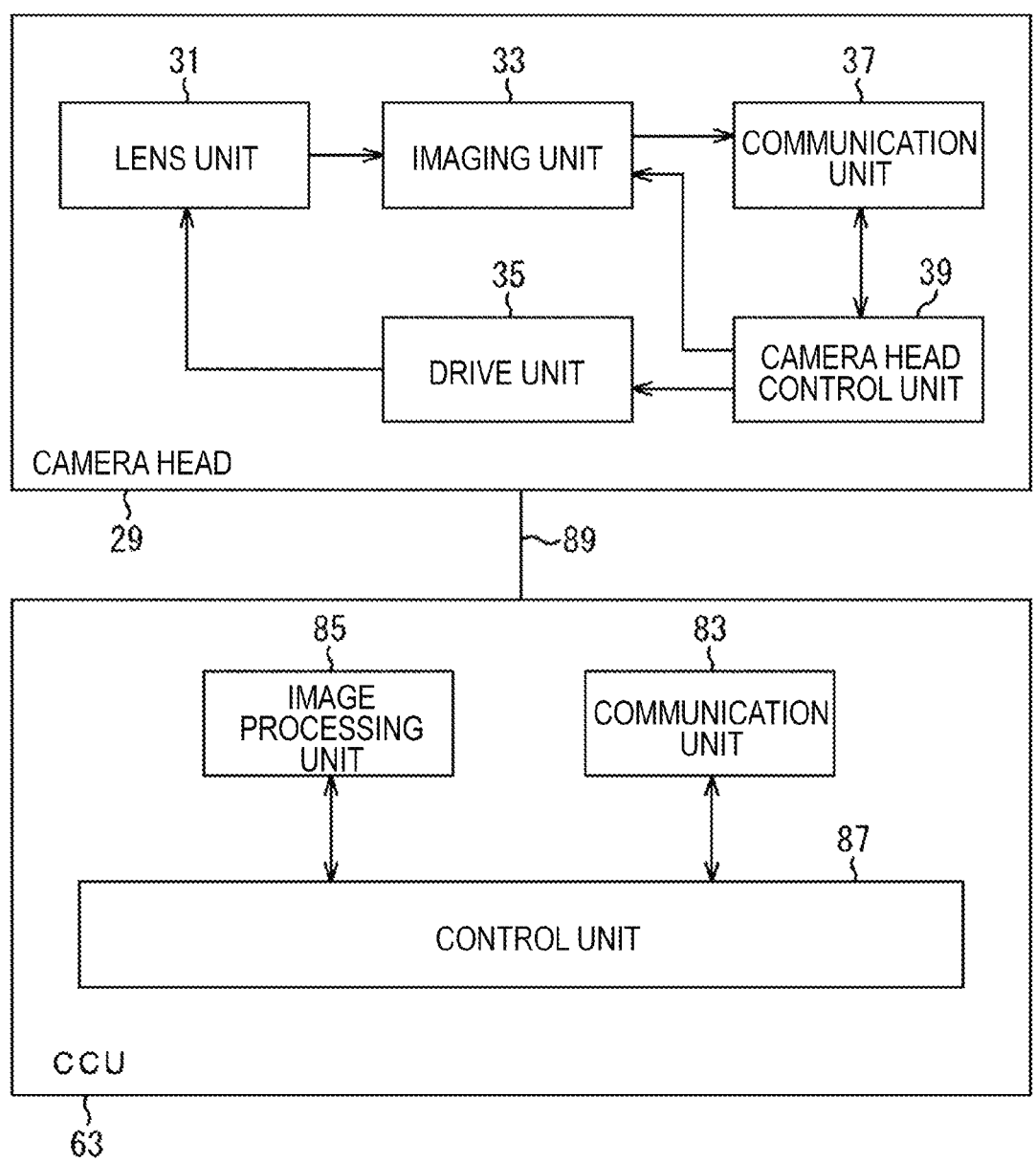
FIG. 4 is a block diagram illustrating an example of a functional configuration of a camera head and a CCU.

Next, with reference to FIG. 4, functions will be described in more detail of the camera head 29 of the endoscope 25 and the CCU 63. FIG. 4 is a block diagram illustrating an example of a functional configuration of the camera head 29 and the CCU 63.

As illustrated in FIG. 4, the camera head 29 includes, as its functions, a lens unit 31, an imaging unit 33, a drive unit 35, a communication unit 37, and a camera head control unit 39. Furthermore, the CCU 63 includes, as its functions, a communication unit 83, an image processing unit 85, and a control unit 87. The camera head 29 and the CCU 63 are communicably connected to each other by a transmission cable 89.

First, the functional configuration will be described of the camera head 29. The lens unit 31 is an optical system provided at a connection portion with the lens barrel 27. The observation light taken in from the distal end of the lens barrel 27 is guided to the camera head 29 and is incident on the lens unit 31. The lens unit 31 includes a plurality of lenses combined including a zoom lens and a focus lens. Optical characteristics of the lens unit 31 are adjusted so that the observation light is focused on the light receiving surface of the imaging element of the imaging unit 33. Furthermore, positions on the optical axis of the zoom lens and the focus lens are movable to adjust the magnification and focus of a captured image.

The imaging unit 33 includes an imaging element, and is arranged at the subsequent stage of the lens unit 31. The observation light passing through the lens unit 31 is focused on the light receiving surface of the imaging element, and an image signal corresponding to the observation image is generated by photoelectric conversion. The image signal generated by the imaging unit 33 is provided to the communication unit 37.

As the imaging element constituting the imaging unit 33, an element is used capable of color imaging having a Bayer array, for example, a complementary metal oxide semiconductor (CMOS) image sensor, or the like. Note that, as the imaging element, an element may be used compatible with imaging of the high-resolution image of greater than or equal to 4K, for example. The image of the surgical portion is obtained with high resolution, whereby the surgeon 91 can grasp a state of the surgical portion in more detail, and can perform the surgery more smoothly.

Furthermore, the imaging element constituting the imaging unit 33 includes a pair of imaging elements for acquiring image signals for the right-eye and left-eye to cope with 3D display. The 3D display is performed, whereby the surgeon 91 can grasp the depth of living tissue in the surgical portion more accurately. Note that, in a case where the imaging unit 33 includes the multi-chip type, a plurality of systems of the lens units 31 is provided corresponding to respective imaging elements.

Furthermore, the imaging unit 33 does not necessarily have to be provided in the camera head 29. For example, the imaging unit 33 may be provided immediately after the objective lens, inside the lens barrel 27.

The drive unit 35 includes an actuator and moves the zoom lens and the focus lens of the lens unit 31 by a predetermined distance along the optical axis by control of the camera head control unit 39. As a result, the magnification and focus of the captured image by the imaging unit 33 can be appropriately adjusted.

The communication unit 37 includes a communication device for transmitting/receiving various types of information to/from the CCU 63. The communication unit 37 transmits the image signal obtained from the imaging unit 33 as RAW data to the CCU 63 via the transmission cable 89. At this time, to display the captured image of the surgical portion with low latency, the image signal is preferably transmitted by optical communication. This is because it is required that a moving image of the surgical portion is displayed in real time as much as possible for safer and more reliable surgery since the surgeon 91 performs the surgery while observing a state of the affected part with the captured image during the surgery. In a case where optical communication is performed, the communication unit 37 is provided with a photoelectric conversion module that converts an electric signal into an optical signal. The image signal is converted into an optical signal by the photoelectric conversion module, and then transmitted to the CCU 63 via the transmission cable 89.

Furthermore, the communication unit 37 receives the control signal for controlling the drive of the camera head 29 from the CCU 63. The control signal includes information regarding imaging conditions, for example, information that specifies the frame rate of the captured image, information that specifies the exposure value at the time of imaging, and/or information that specifies the magnification and focus of the captured image, and the like. The communication unit 37 provides the received control signal to the camera head control unit 39. Note that, the control signal from the CCU 63 may also be transmitted by optical communication. In this case, the communication unit 37 is provided with a photoelectric conversion module that converts an optical signal into an electric signal, and the control signal is converted into an electric signal by the photoelectric conversion module and then provided to the camera head control unit 39.

Note that, the above-described imaging conditions such as the frame rate, the exposure value, the magnification, and the focus are automatically set by the control unit 87 of the CCU 63 on the basis of the image signal acquired. That is, a so-called auto exposure (AE) function, auto-focus (AF) function, and auto white balance (AWB) function are installed in the endoscope 25.

The camera head control unit 39 controls the drive of the camera head 29 on the basis of the control signal from the CCU 63 received via the communication unit 37. For example, the camera head control unit 39 controls drive of the imaging element of the imaging unit 33 on the basis of the information that specifies the frame rate of the captured image and/or the information that specifies the exposure at the time of imaging. Furthermore, for example, the camera head control unit 39 appropriately moves the zoom lens and focus lens of the lens unit 31 via the drive unit 35 on the basis of the information that specifies the magnification and focus of the captured image. The camera head control unit 39 may further have a function of storing information for identifying the lens barrel 27 and the camera head 29.

Note that, the camera head 29 can be made to have resistance to autoclave sterilization by arranging the lens unit 31, the imaging unit 33, and the like in a sealed structure with high airtightness and waterproofness.

Next, the functional configuration will be described of the CCU 63. The communication unit 83 includes a communication device for transmitting/receiving various types of information to/from the camera head 29. The communication unit 83 receives the image signal transmitted via the transmission cable 89 from the camera head 29. Here, as described above, the image signal can be suitably transmitted by optical communication. In this case, to be adaptable to optical communication, the communication unit 83 is provided with a photoelectric conversion module that converts an optical signal into an electric signal. The communication unit 83 provides the image signal converted into the electric signal to the image processing unit 85.

Furthermore, the communication unit 83 transmits the control signal for controlling the drive of the camera head 29 to the camera head 29. The control signal may also be transmitted by optical communication.

The image processing unit 85 performs various types of image processing on the image signal that is RAW data transmitted from the camera head 29. Examples of the image processing includes various types of known signal processing, for example, development processing, image quality enhancement processing (such as band enhancement processing, super-resolution processing, noise reduction (NR) processing and/or camera shake correction processing), and/or enlargement processing (electronic zoom processing), and the like. Furthermore, the image processing unit 85 performs detection processing on the image signal for performing AE, AF, and AWB.

The image processing unit 85 includes a processor such as a CPU or GPU, and the image processing and detection processing described above are performed by the processor operating in accordance with a predetermined program.

Note that, in a case where the image processing unit 85 includes a plurality of GPUs, the image processing unit 85 appropriately divides information related to the image signal and performs the image processing in parallel by the plurality of GPUs.

The control unit 87 performs various controls regarding imaging of the surgical portion by the endoscope 25 and display of the captured image. For example, the control unit 87 generates the control signal for controlling the drive of the camera head 29. Here, in a case where the imaging conditions are input by the user, the control unit 87 generates the control signal on the basis of the input by the user. Furthermore, in a case where the AE function, the AF function, and the AWB function are installed in the endoscope 25, the control unit 87 generates the control signal by appropriately calculating the optimum exposure value, focal length, and white balance depending on a result of the detection processing by the image processing unit 85.

Furthermore, the control unit 87 causes the display device 65 to display the image of the surgical portion on the basis of the image signal on which the image processing is performed by the image processing unit 85. At this time, the control unit 87 recognizes various objects in the surgical portion image by using various image recognition technologies. For example, the control unit 87 detects color, a shape of an edge, and the like of the object included in the surgical portion image, thereby being able to recognize the surgical tools 41 such as the forceps 47, a specific body part, bleeding, mist at the time of using the energy treatment tool 45, or the like. When causing the display device 65 to display the image of the surgical portion, the control unit 87 causes the display device 65 to superimpose and display various types of surgery assistance information on the image of the surgical portion by using the recognition result. The surgery assistance information is superimposed and displayed, and presented to the surgeon 91, whereby the surgery can be performed more safely and reliably.

The transmission cable 89 connecting the camera head 29 and the CCU 63 together is an electric signal cable adaptable to communication of electric signals, an optical fiber adaptable to optical communication, or a composite cable thereof.

In this example, communication is performed by wire using the transmission cable 89, but communication between the camera head 29 and the CCU 63 may be performed wirelessly. In a case where the communication between the two is performed wirelessly, it is not necessary to install the transmission cable 89 in the operation room, so that a situation is eliminated where the movement of the medical staff in the operation room is hindered by the transmission cable 89.

2. Endoscopic Surgical System to which the Present Technology is Applied

Next, with reference to FIG. 5, a functional configuration example will be described of an endoscopic surgical system to which the present technology is applied.

Figure 5:
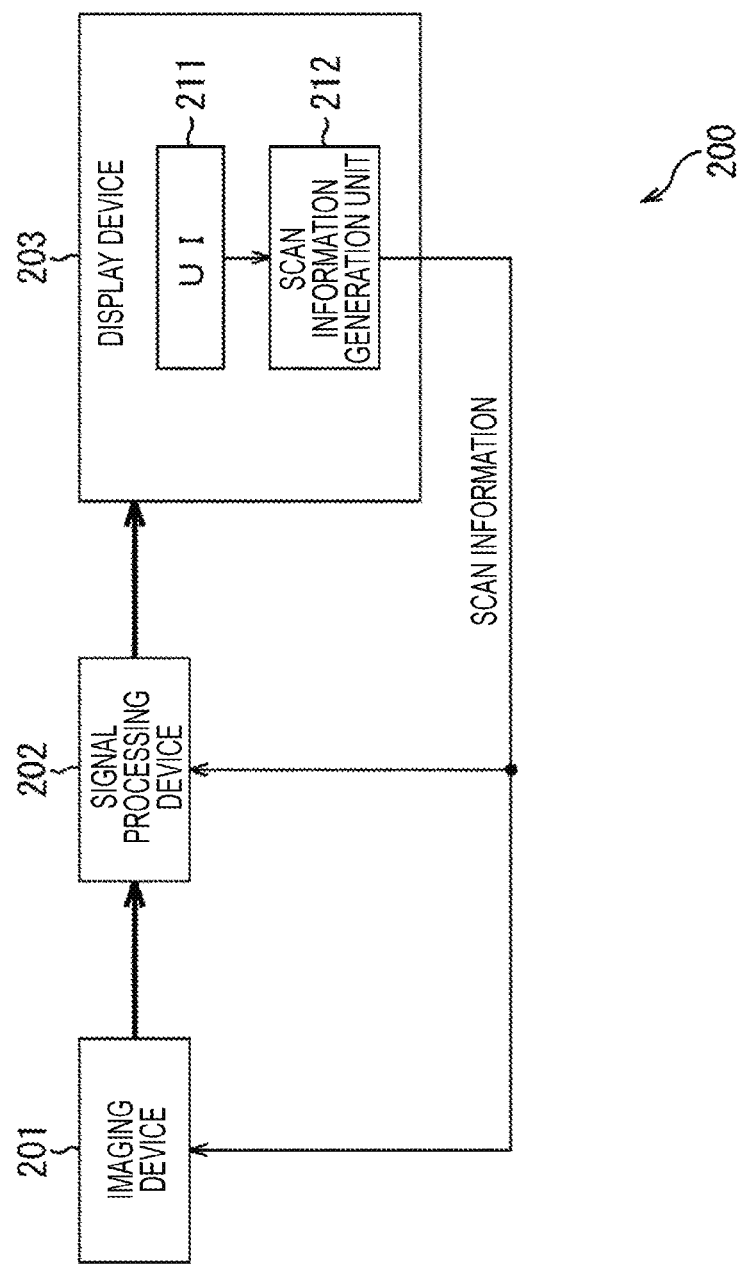
FIG. 5 is a block diagram illustrating a functional configuration example of an endoscopic surgical system to which the present technology is applied.

An endoscopic surgical system 200 of FIG. 5 includes an imaging device 201, a signal processing device 202, and a display device 203.

The imaging device 201 corresponds to the camera head 29 described above and, as a surgical imaging device, acquires data (image signal) of a captured image by imaging a living body. The acquired image signal is transmitted to the signal processing device 202. Here, as the captured image, a surgical portion image (a surgical image in which the inside of the living body is captured) is acquired that is an image of a surgical portion in a body cavity.

The signal processing device 202 corresponds to the CCU 63 described above, and performs predetermined signal processing on the image signal transmitted from the imaging device 201. The image signal on which the signal processing is performed is transmitted to the display device 203.

The display device 203 corresponds to the display device 65 described above, and displays the captured image on the basis of the image signal transmitted from the signal processing device 202.

The display device 203 includes a user interface (UI) 211 that accepts user's operation. For example, the UI 211 accepts specification of the top and bottom direction of the captured image to be displayed on the display device 203.

Figure 6:
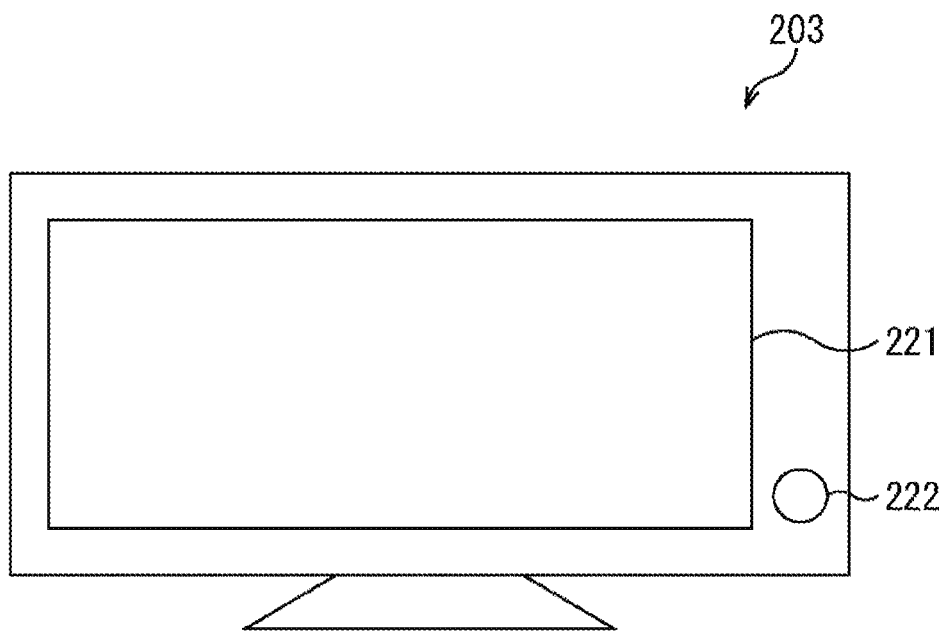
FIG. 6 is a diagram illustrating an appearance configuration example of a display device.

FIG. 6 illustrates an appearance configuration example of the display device 203.

As illustrated in FIG. 6, the display device 203 includes a display unit 221 and an operation button 222. The display unit 221 displays the captured image that is captured by the imaging device 201 and on which the signal processing is performed by the signal processing device 202. The operation button 222 is one of the UIs 211 described above, and accepts the specification of the top and bottom direction of the captured image to be displayed on the display unit 221 by being operated by the user.

Note that, in addition to providing the physical operation button 222 as the UI 211, the display unit 221 may be configured as a touch panel, and a button for accepting the specification of the top and bottom direction may be displayed on the display unit 221.

Referring back to FIG. 5, the display device 203 further includes a scan information generation unit 212. The scan information generation unit 212 generates scan information indicating a scan order of the captured image on the basis of the specification of the top and bottom direction accepted by the UI 211. The generated scan information is supplied to the imaging device 201 and the signal processing device 202.

When the scan information is supplied from the scan information generation unit 212, the imaging device 201 generates the captured image on the basis of the scan information. When the scan information is supplied from the scan information generation unit 212, the signal processing device 202 performs signal processing on the captured image on the basis of the scan information. Furthermore, when the scan information is generated by the scan information generation unit 212, the display device 203 displays the captured image on the basis of the scan information.

For example, in endoscopic surgery, in a case where a direction of the top and bottom of an image to be displayed on a display device is opposite to a direction of the top and bottom determined by the direction of gravity, depending on a direction of the top and bottom of an endoscope inserted into an abdominal cavity, the display device has conventionally inverted and displayed the image. Note that, here, "invert and display" means that the image is rotated by 180 degrees and displayed.

Figure 7:
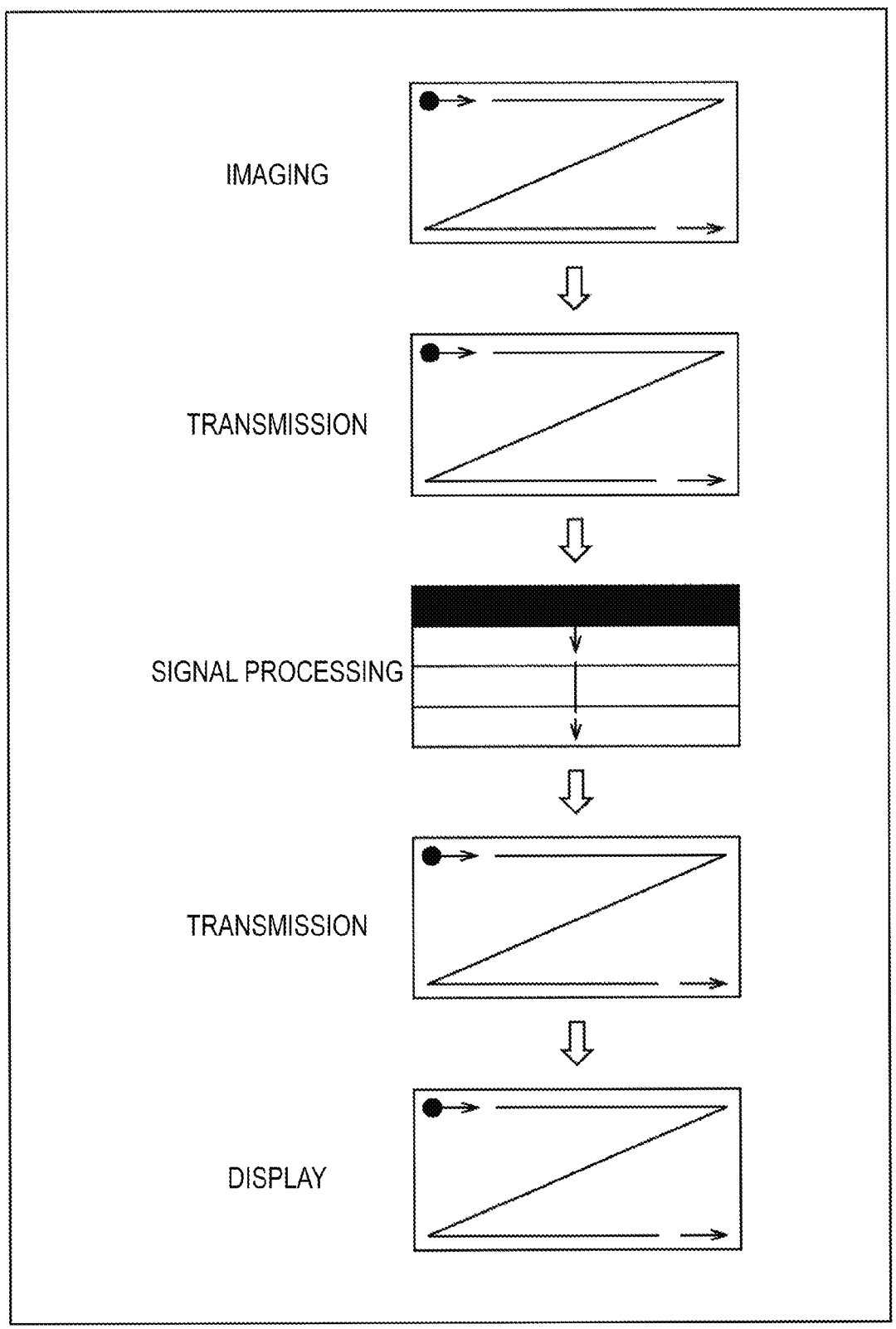
FIG. 7 is a diagram for explaining a flow of conventional image inversion.

FIG. 7 illustrates a flow of image inversion in a conventional endoscopic surgical system in a case where the direction of the top and bottom of the image to be displayed on the display device is opposite to the direction of the top and bottom determined by the direction of gravity.

First, as illustrated in the first and second stages from the top of FIG. 7, the imaging device acquires pixel data by scanning from the upper left to the upper right, from the lower left to the lower right of the captured image in a dot sequential manner, and sequentially transmits the pixel data to the signal processing device.

Next, as illustrated in the third and fourth stages of FIG. 7, the signal processing device performs signal processing by scanning from the top to the bottom of the captured image in a block sequential manner, for example, and transmits, to the display device, data of a block in which the signal processing is finished in the dot sequential manner. Here, the signal processing is performed in the block sequential manner, but the signal processing may be performed in a line sequential manner or the dot sequential manner.

Here, in the following, the scan order from the upper left to the upper right, from the lower left to the lower right, or the scan order from the top to the bottom is referred to as a forward direction scan order.

Then, as illustrated in the fifth stage of FIG. 7, the display device performs display by scanning from the upper left to the upper right, from the lower left to the lower right of the captured image in the dot sequential manner.

Transmission of the image from the imaging device to the display device is performed serially as described above. Therefore, to invert and display the image on the display device, it has been necessary to store one image in a memory in the display device. Specifically, the signal processing device starts transmission sequentially from data on the lower side in the vertical direction of the image to be inverted and displayed on the display device. The display device wants to start scanning from data on the upper side in the vertical direction of the image to be inverted and displayed, but the data is transmitted last from the signal processing device.

Figure 8:
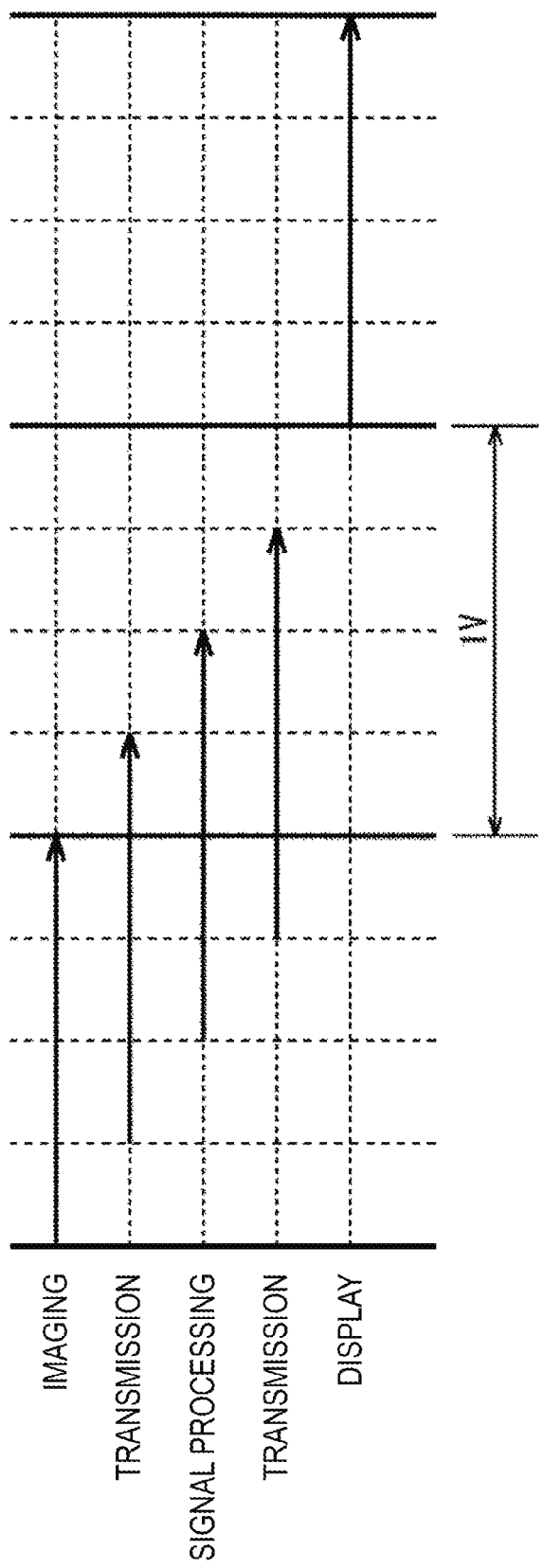
FIG. 8 is a diagram for explaining latency in the conventional image inversion.

Thus, it has been necessary for a conventional display device having such an inversion display function to perform scanning for display after waiting for completion of storage of one image in the memory. In other words, as illustrated in FIG. 8, a latency has occurred of about transmission time (1V) for one screen from the completion of scanning for imaging until the start of scanning for display.

Furthermore, although the latency can be reduced by increasing the frame rate, there is a demerit that power consumption and cost are increased. This demerit increases as the frame rate and resolution increase.

On the other hand, in the endoscopic surgical system of the present technology, scan information is generated on the basis of the specification of the top and bottom direction of the captured image to be displayed on the display device 203, and respective scans for imaging, signal processing, and display are performed in the scan order indicated by the scan information.

Figure 9:
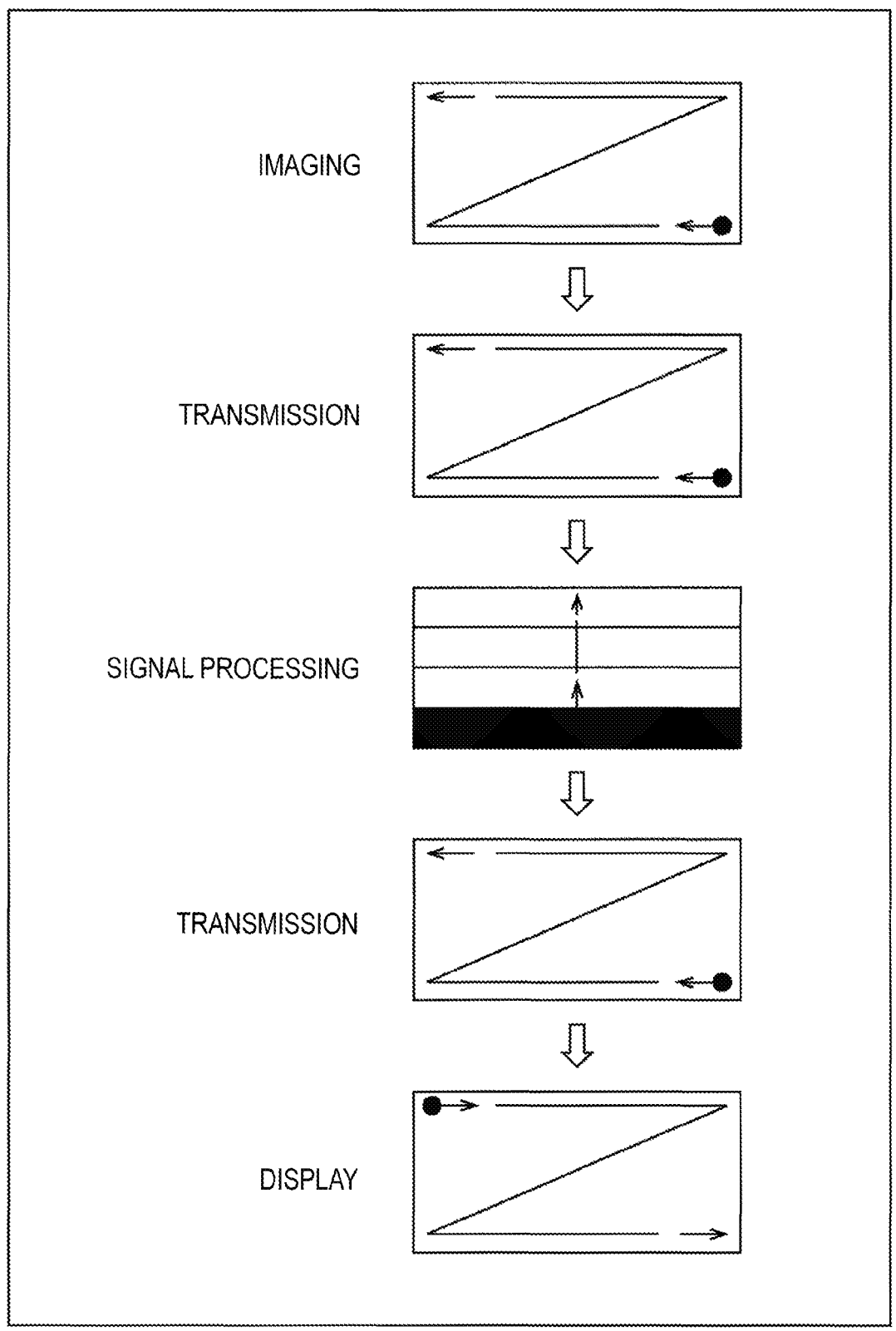
FIG. 9 is a diagram for explaining a flow of image inversion of the present technology.

FIG. 9 illustrates a flow of image inversion in the endoscopic surgical system of the present technology in a case where inversion is specified in the top and bottom direction of the captured image to be displayed in the display device 203.

First, on the basis of the scan information, the imaging device 201 performs scanning in a scan order opposite to the forward direction scan order (hereinafter, referred to as a backward direction scan order as appropriate). In other words, as illustrated in the first and second stages from the top of FIG. 9, the imaging device 201 acquires pixel data by scanning from the lower right to the lower left, from the upper right to the upper left of the captured image in the dot sequential manner, and sequentially transmits the pixel data to the signal processing device.

Next, the signal processing device 202 performs scanning in the backward direction scan order on the basis of the scan information. Here, as illustrated in the third and fourth stages of FIG. 9, the signal processing device 202 performs signal processing by scanning from the bottom to the top of the captured image in the block sequential manner, for example, and transmits, to the display device, data of a block in which the signal processing is finished in the dot sequential manner.

Then, the display device 203 performs scanning in the forward direction scan order on the basis of the scan information. In other words, as illustrated in the fifth stage of FIG. 9, the display device 203 performs display by scanning from the upper left to the upper right, from the lower left to the lower right of the captured image in the dot sequential manner.

At this time, the signal processing device 202 starts transmission sequentially from data on the upper side in the vertical direction of the image to be inverted and displayed on the display device 203. Thus, the display device 203 can start scanning from the data on the upper side in the vertical direction of the image to be inverted and displayed.

Figure 10:
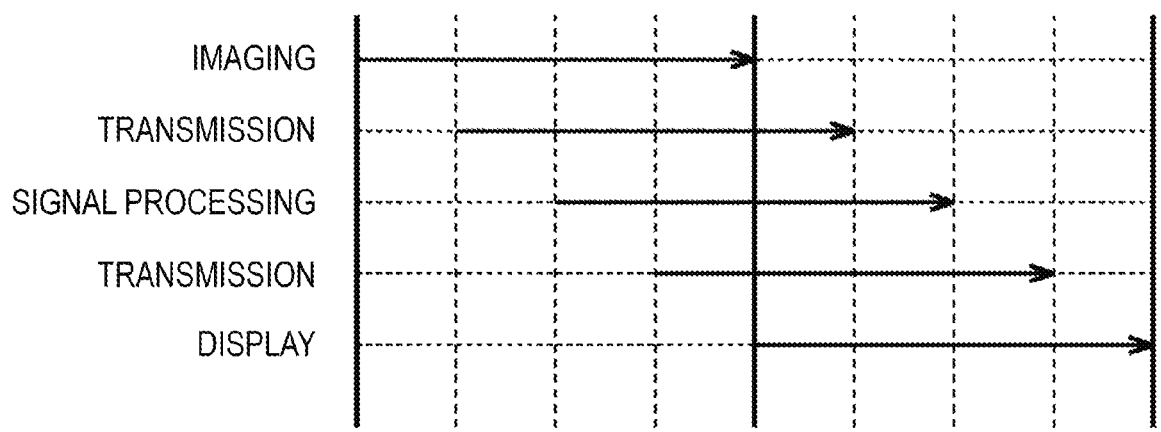
FIG. 10 is a diagram for explaining latency in the image inversion of the present technology.

As described above, according to the endoscopic surgical system 200 of FIG. 5, respective scan orders for imaging, signal processing, and display are determined depending on the top and bottom direction of the captured image to be displayed on the display device 203, so that the display device 203 can perform scanning for display without waiting for completion of storage of one image in the memory. As a result, as illustrated in FIG. 10, the latency from imaging to display can be reduced as compared with the conventional one illustrated in FIG. 8.

Furthermore, since the latency can be reduced without increasing the frame rate, the demerit can be avoided that the power consumption and the cost are increased.

Moreover, in the endoscopic surgical system 200 described above, the respective scan orders for imaging, signal processing, and display are determined depending on the top and bottom direction of the captured image to be displayed on the display device 203, whereby a function can be implemented of vertically mirror-inverting and displaying the captured image, in addition to a function of rotating by 180 degrees and displaying the captured image. The latency from imaging to display can be reduced even in such a configuration.

Note that, in a case where the latency of 1V described above is allowed, the display device 203 may have the conventional inversion display function (in other words, perform scanning for display after waiting for completion of storage of one image in the memory). Furthermore, in this case, the display device 203 may have, as the inversion display function, the function of vertically mirror-inverting and displaying the captured image, in addition to the function of rotating by 180 degrees and displaying the captured image.

3. First Modification

Figure 11:
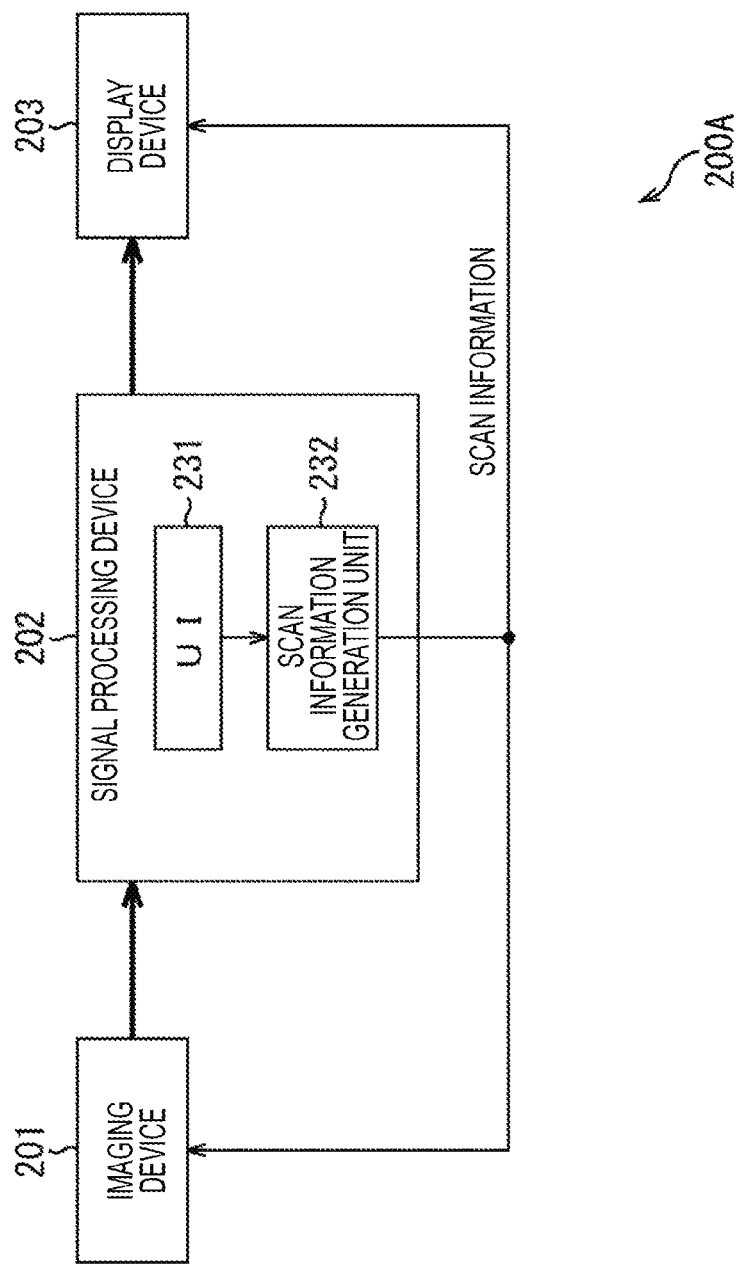
FIG. 11 is a block diagram illustrating another functional configuration example of the endoscopic surgical system.

FIG. 11 is a diagram illustrating a first modification of the endoscopic surgical system to which the present technology is applied.

In an endoscopic surgical system 200A of FIG. 11, the signal processing device 202 includes a UI 231 and a scan information generation unit 232. The UI 231 and the scan information generation unit 232 respectively have the same functions as those of the UI 211 and the scan information generation unit 212 of FIG. 5.

Thus, according to the endoscopic surgical system 200A of FIG. 11, functions and effects can be achieved similar to those of the endoscopic surgical system 200 of FIG. 5.

4. Second Modification

Figure 12:
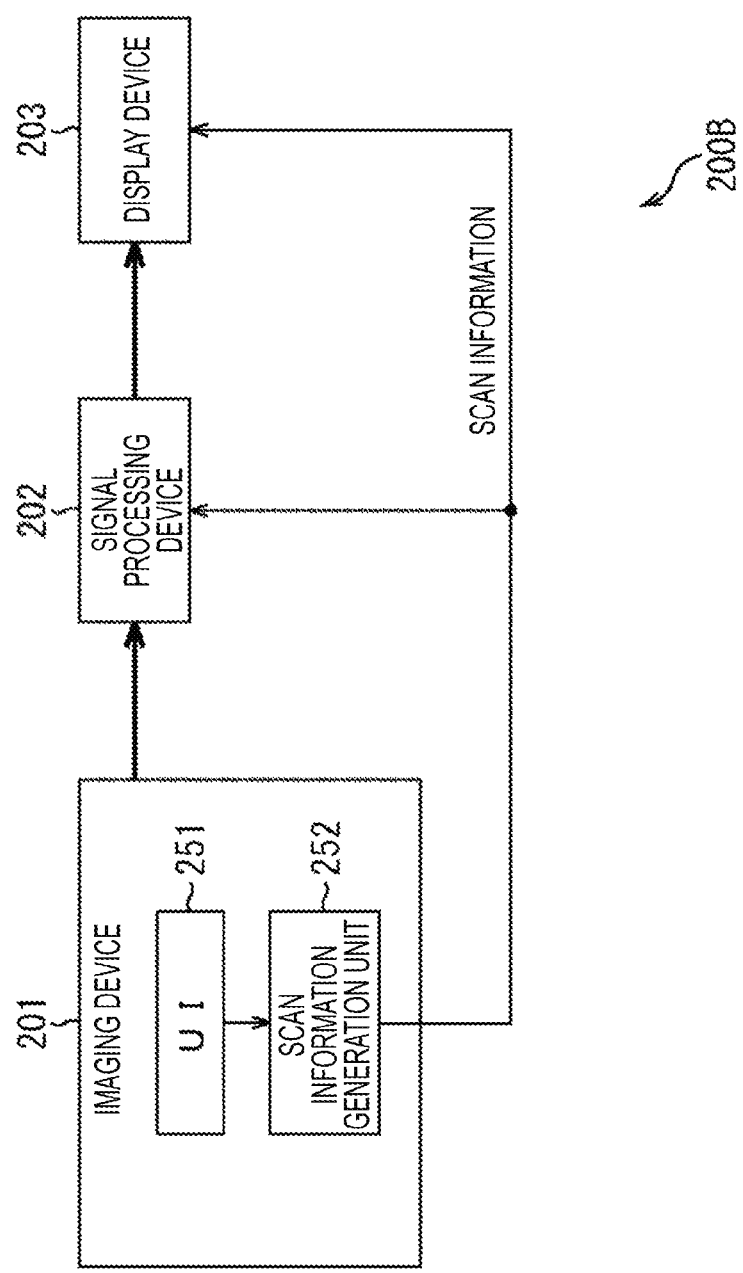
FIG. 12 is a block diagram illustrating yet another functional configuration example of the endoscopic surgical system.

FIG. 12 is a diagram illustrating a second modification of the endoscopic surgical system to which the present technology is applied.

In an endoscopic surgical system 200B of FIG. 12, the imaging device 201 includes a UI 251 and a scan information generation unit 252. The UI 251 and the scan information generation unit 252 respectively have the same functions as those of the UI 211 and the scan information generation unit 212 of FIG. 5.

Thus, according to the endoscopic surgical system 200B of FIG. 12, functions and effects can be achieved similar to those of the endoscopic surgical system 200 of FIG. 5.

5. Third Modification

Figure 13:
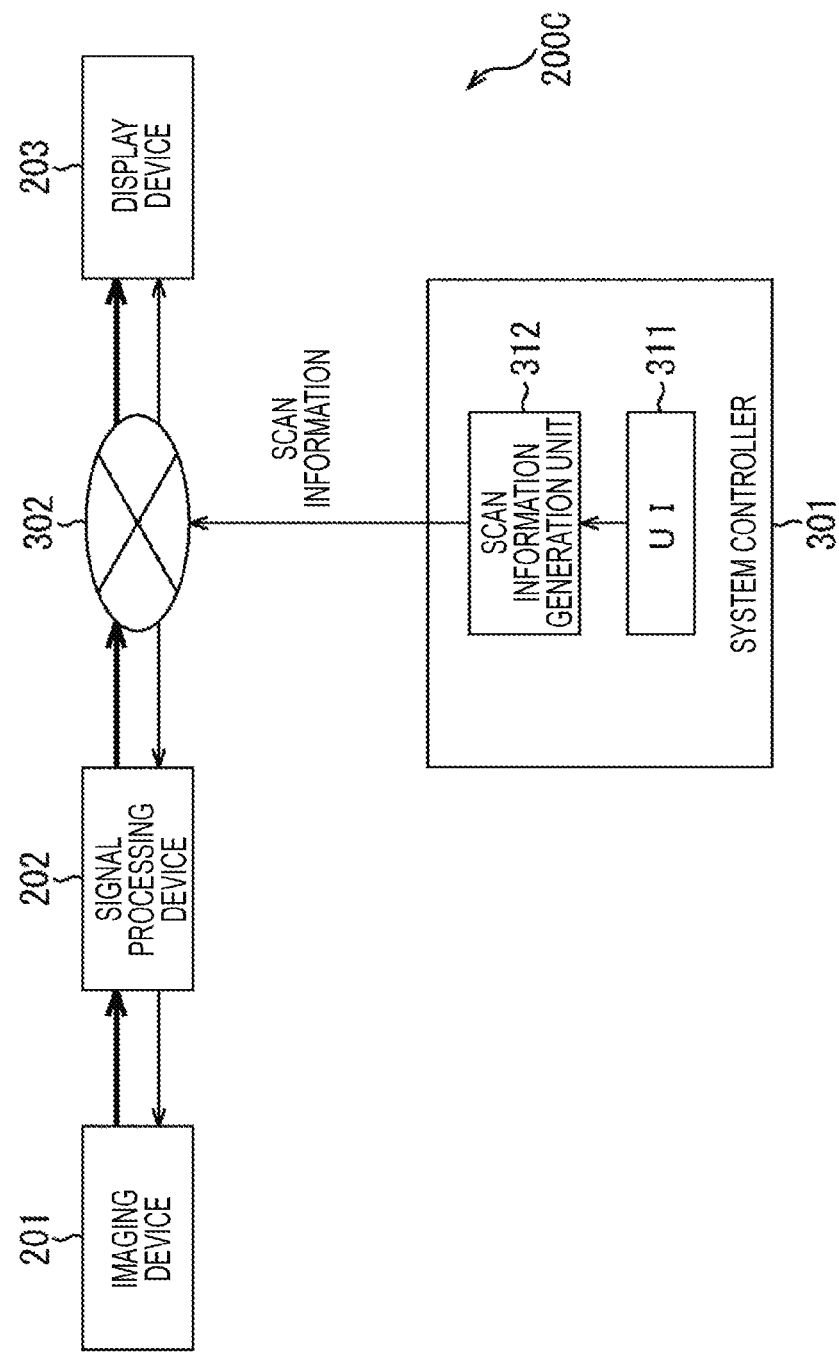
FIG. 13 is a block diagram illustrating yet another functional configuration example of the endoscopic surgical system.

FIG. 13 is a diagram illustrating a third modification of the endoscopic surgical system to which the present technology is applied.

In an endoscopic surgical system 200C of FIG. 13, in addition to devices from the imaging device 201 to the display device 203, a system controller 301 is provided. The system controller 301 corresponds to, for example, the audiovisual controller 17 in the operation room system 10 described above, and controls operations of the devices from the imaging device 201 to the display device 203. In the example of FIG. 13, the signal processing device 202, the display device 203, and the system controller 301 are connected to each other via a network 302.

The system controller 301 includes a UI 311 and a scan information generation unit 312. The UI 311 and the scan information generation unit 312 respectively have the same functions as those of the UI 211 and the scan information generation unit 212 of FIG. 5. Note that, in the example of FIG. 13, the scan information generated by the scan information generation unit 312 is supplied to the signal processing device 202 and the display device 203 via the network 302, and to the imaging device 201 via the network 302 and the signal processing device 202.

Thus, according to the endoscopic surgical system 200C of FIG. 13, functions and effects can be achieved similar to those of the endoscopic surgical system 200 of FIG. 5.

6. Fourth Modification

Figure 14:
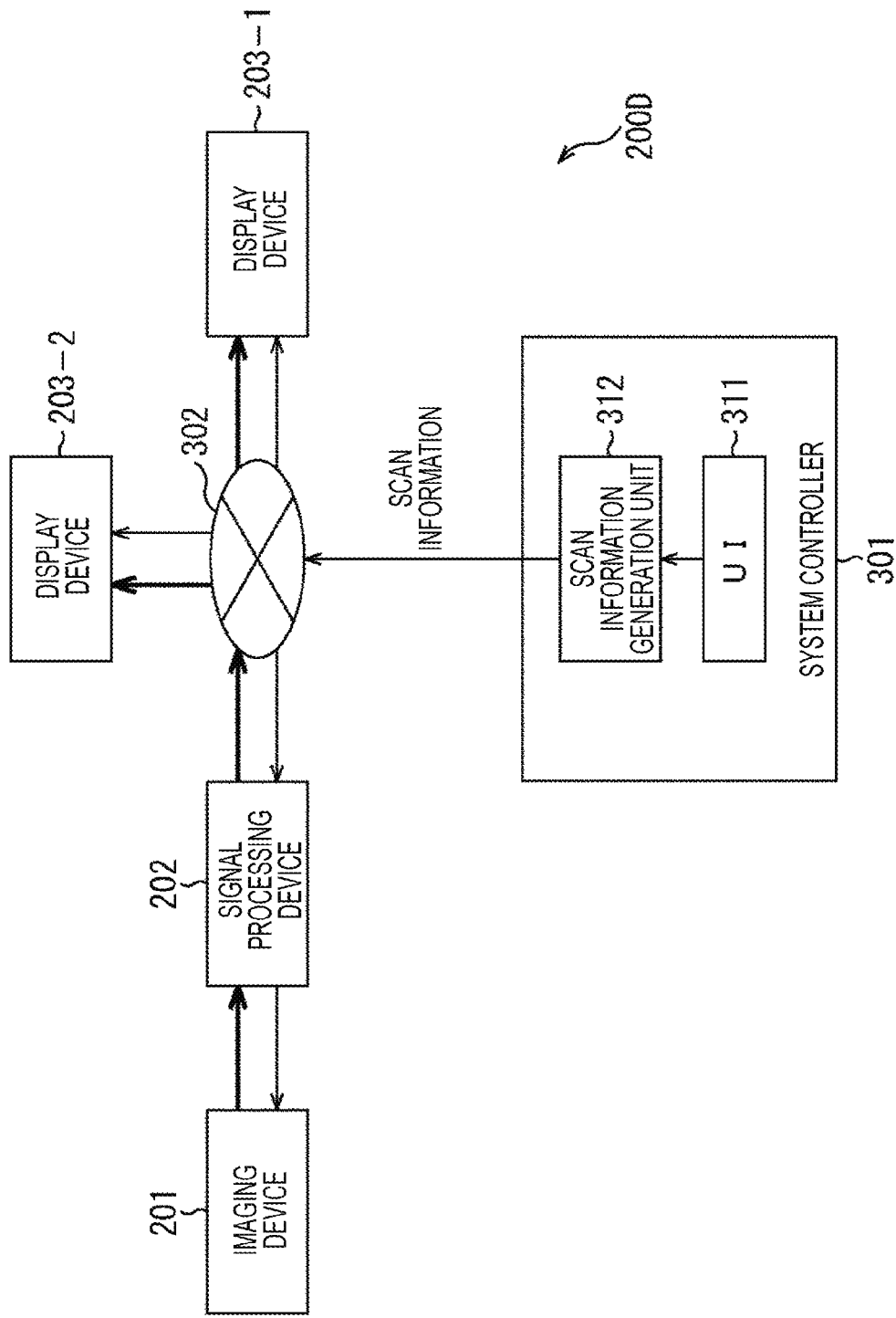
FIG. 14 is a block diagram illustrating yet another functional configuration example of the endoscopic surgical system.

FIG. 14 is a diagram illustrating a fourth modification of the endoscopic surgical system to which the present technology is applied.

In an endoscopic surgical system 200D of FIG. 14, two display devices 203-1 and 203-2 are provided. In FIG. 14, the UI 311 of the system controller 301 accepts specification of the top and bottom direction of the captured image to be displayed on each of the display devices 203-1 and 203-2.

Figure 15:
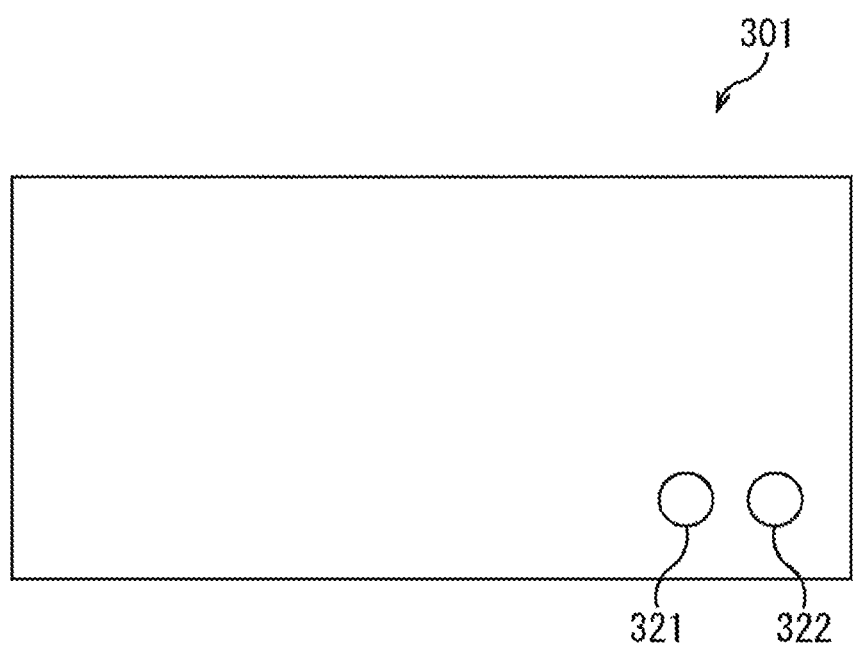
FIG. 15 is a diagram illustrating an appearance configuration example of a system controller.

FIG. 15 illustrates an appearance configuration example of the system controller 301.

As illustrated in FIG. 15, the system controller 301 includes operation buttons 321 and 322. The operation button 321 is one of the UIs 311 described above, and accepts the specification of the top and bottom direction of the captured image to be displayed on the display device 203-1 by being operated by the user. The operation button 322 is also one of the UIs 311 described above, and accepts the specification of the top and bottom direction of the captured image to be displayed on the display device 203-2 by being operated by the user.

Note that, in addition to providing the physical operation buttons 321 and 322 as the UIs 311, a display unit including a touch panel may be provided in the system controller 301, and buttons for accepting the specifications of the top and bottom directions may be displayed on the display unit. Furthermore, the UI 311 may be provided on the operation screen (FIG. 2) on the centralized operation panel 21.

Here, with reference to FIG. 16, a relationship will be described between a scan order of the imaging device 201 and display latencies in the display devices 203-1 and 203-2 depending on inversion specifications of the top and bottom directions of the captured images to be displayed on the respective display devices 203-1 and 203-2.

(Case where there is No Inversion Specification of Top and Bottom Direction for Either of Display Device 203-1 or 203-2)

In a case where the scan order of the imaging device 201 is the forward direction, the display devices 203-1 and 203-2 only need to display the captured images in the order scanned by the imaging device 201, and can perform scanning for display without waiting for completion of storage of one image in the memory, that is, with a latency of 0V.

(Case where there is No Inversion Specification of Top and Bottom Direction of Display Device 203-1, and there is Inversion Specification of Top and Bottom Direction of Display Device 203-2)

In a case where the scan order of the imaging device 201 is the forward direction, the display device 203-1 only needs to display the captured image in the order scanned by the imaging device 201, and can perform scanning for display with a latency of 0V.

On the other hand, since the display device 203-2 displays the captured image in the reverse order of the order scanned by the imaging device 201, it is necessary to perform scanning for display after waiting for completion of storage of one image in the memory by the conventional inversion display function. Thus, a latency of 1V occurs.

Note that, since the display timing of the captured image is shifted by 1V between the display device 203-1 and the display device 203-2, the display device 203-1 may intentionally display the display image with a delay of 1V.

(Case where there is Inversion Specification of Top and Bottom Direction of Display Device 203-1, and there is No Inversion Specification of Top and Bottom Direction of Display Device 203-2)

In a case where the scan order of the imaging device 201 is the forward direction, the display device 203-2 only needs to display the captured image in the order scanned by the imaging device 201, and can perform scanning for display with a latency of 0V.

On the other hand, since the display device 203-1 displays the captured image in the reverse order of the order scanned by the imaging device 201, it is necessary to perform scanning for display after waiting for completion of storage of one image in the memory by the conventional inversion display function. Thus, a latency of 1V occurs.

Note that, since the display timing of the captured image is shifted by 1V between the display device 203-1 and the display device 203-2, the display device 203-2 may intentionally display the display image with a delay of 1V.

(Case where there is Inversion Specification of Top and Bottom Direction for Both of Display Devices 203-1 and 203-2)

In a case where the scan order of the imaging device 201 is the backward direction, the display devices 203-1 and 203-2 only need to display captured images in the order scanned by the imaging device 201, and can perform scanning for display with a latency of 0V.

As described above, according to the endoscopic surgical system 200D of FIG. 14, the latency of each display device can be adjusted depending on the inversion instructions of the top and bottom direction in the two display devices and the scan order of the imaging device.

7. Fifth Modification

Figure 17:
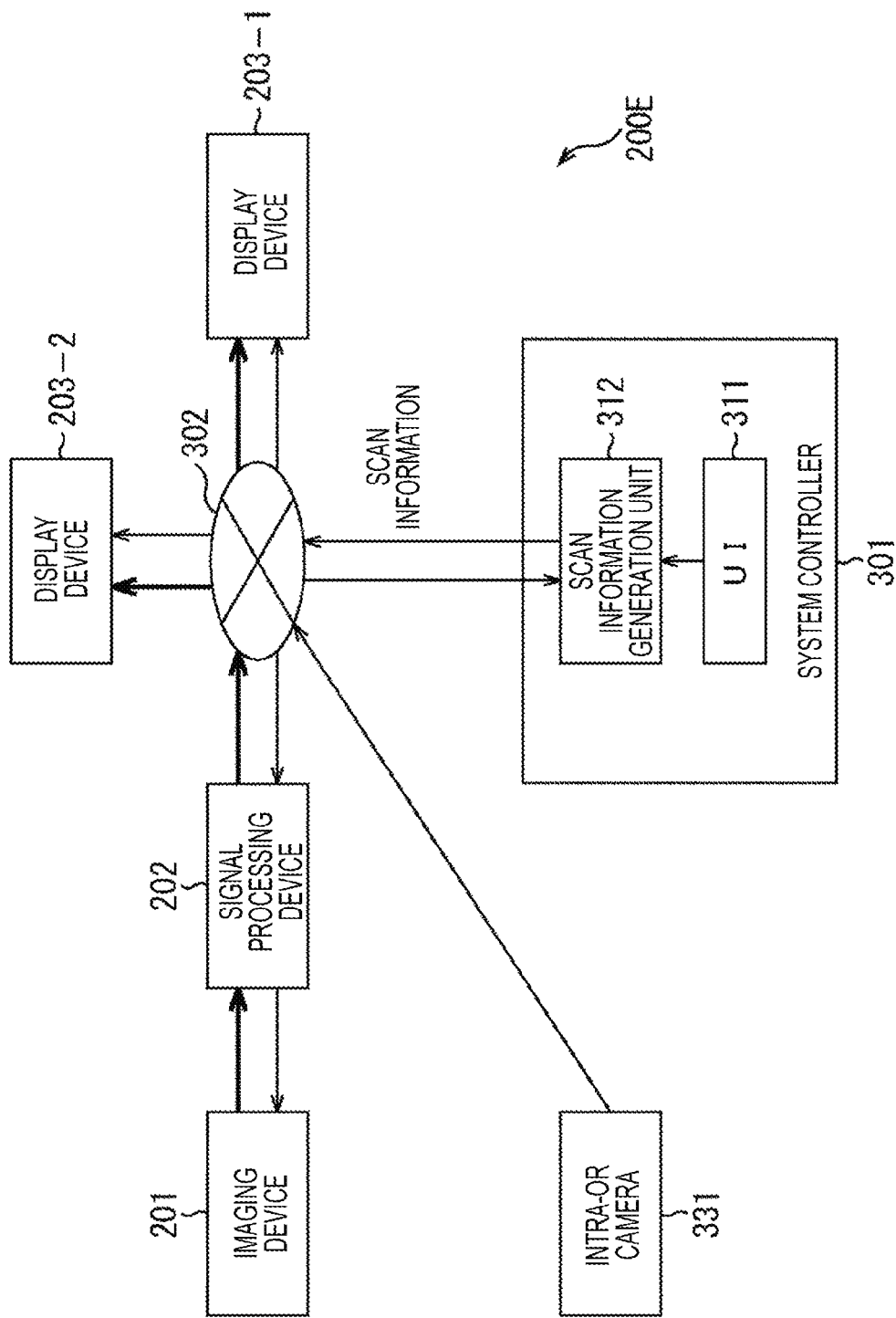
FIG. 17 is a block diagram illustrating yet another functional configuration example of the endoscopic surgical system.

FIG. 17 is a diagram illustrating a fifth modification of the endoscopic surgical system to which the present technology is applied.

In an endoscopic surgical system 200E of FIG. 17, an intra-operation room (OR) camera 331 is newly provided in addition to the configuration of the endoscopic surgical system 200D of FIG. 14. The intra-OR camera 331 corresponds to, for example, the operation room camera 99 in the operation room system 10 described above, and images a state of the entire operation room. In the example of FIG. 17, the signal processing device 202, the display device 203, the system controller 301, and the intra-OR camera 331 are connected to each other via the network 302.

The scan information generation unit 312 of FIG. 17 detects a positional relationship among the user (surgeon), the imaging device 201, and the display devices 203-1 and 203-2 from an image captured by the intra-OR camera 331, and generates scan information on the basis of the detection result.

As described above, according to the endoscopic surgical system 200E of FIG. 17, respective scan orders for imaging, signal processing, and display can be determined depending on the positional relationship among the surgeon, the imaging device 201, and the display devices 203-1 and 203-2 in the operation room.

8. Sixth Modification

Figure 18:
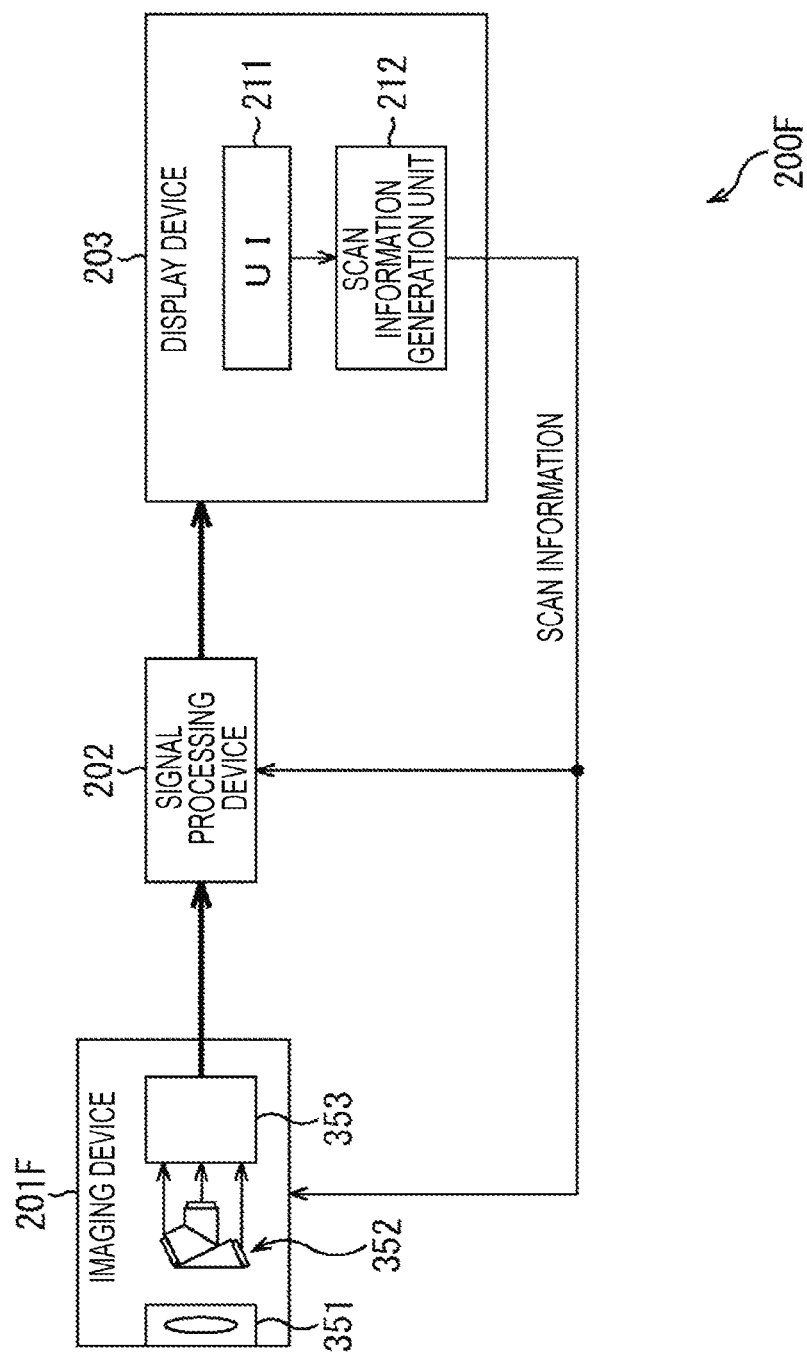
FIG. 18 is a block diagram illustrating yet another functional configuration example of the endoscopic surgical system.

FIG. 18 is a diagram illustrating a sixth modification of the endoscopic surgical system to which the present technology is applied.

In an endoscopic surgical system 200F of FIG. 18, an imaging device 201F is provided instead of the imaging device 201 of the endoscopic surgical system 200 of FIG. 5.

The imaging device 201F is configured as a three-chip camera, and includes an optical block 351, an imaging unit 352, and a preprocessing unit 353.

The optical block 351 includes an imaging lens, a focus mechanism, a shutter mechanism, an aperture mechanism, and the like. The imaging unit 352 includes a color separation prism that separates light incident from the optical block into color components of R, G, and B, and three imaging elements (image sensors) that output electric signals corresponding to respective light intensities of the color components. The preprocessing unit 353 performs predetermined signal processing such as noise reduction, automatic gain control, and A/D conversion on an analog signal from the imaging unit 352, and outputs the signal as digital data.

When scan information is supplied from the scan information generation unit 212, the imaging device 201F generates a captured image on the basis of the scan information.

Specifically, the imaging device 201F performs imaging on the basis of the scan information from the scan information generation unit 212 so that the scan orders for images on the three image sensors are the same as each other. The scan order of each image sensor is determined by a direction in which each image sensor is fixed and the number of times of reflection in an optical path from a subject to the image sensor.

Note that, in the example of FIG. 18, the imaging device 201F is configured as a multi-chip camera, but may be configured as a stereo camera that generates images for the right-eye and left-eye to cope with 3D display. In this case, the imaging device 201F performs imaging on the basis of the scan information from the scan information generation unit 212 so that the scan orders for images on a pair of the image sensors are the same as each other.

9. Seventh Modification

Next, a seventh modification will be described of the endoscopic surgical system to which the present technology is applied.

In this example, the imaging device 201 has a digital zoom function, and partially drives an image sensor during zooming.

Figure 19:
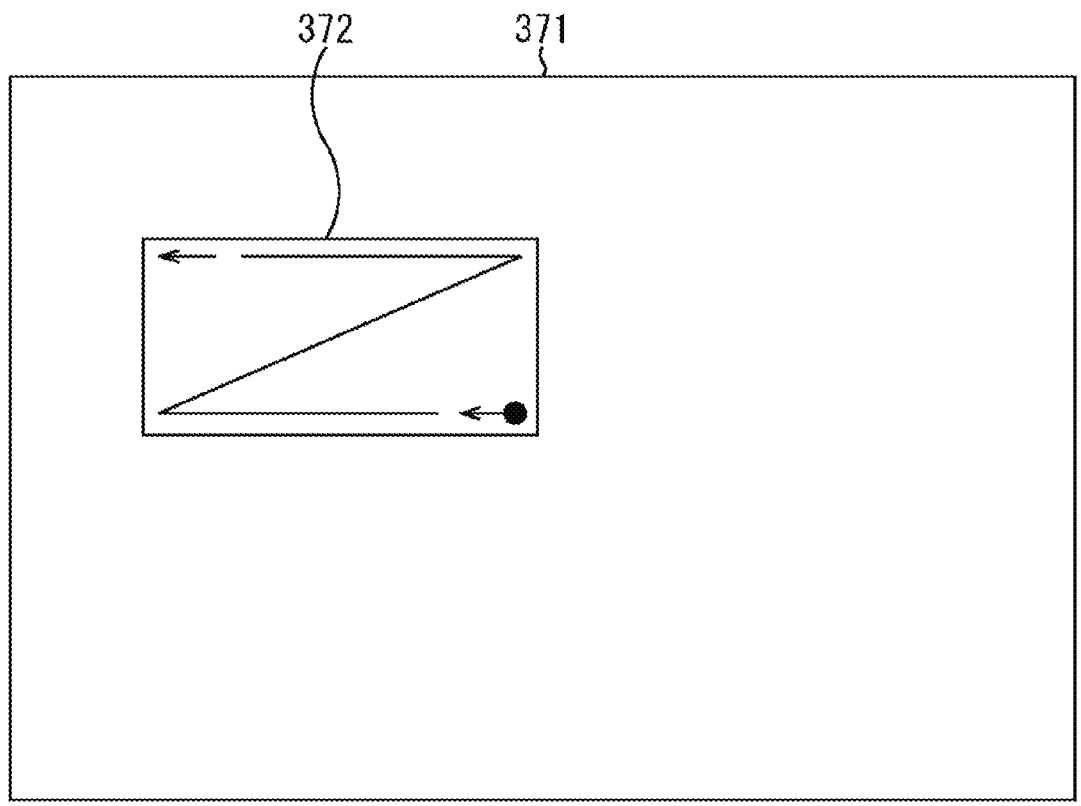
FIG. 19 is a diagram illustrating an example of scanning a zoom area of an image sensor.

FIG. 19 illustrates a pixel area of the image sensor included in the imaging device 201 of this example.

In a case where digital zoom is performed, it is sufficient that a captured image is generated corresponding to a pixel area 372 necessary for zoom display on a pixel area 371 of the image sensor, and data of the captured image is transmitted. At this time, in the pixel area 372, pixel data is acquired in the scan order based on scan information.

With such a configuration, the latency can be reduced compared with a case where data of a captured image corresponding to the entire pixel area 371 is transmitted.

10. Eighth Modification

Next, an eighth modification will be described of the endoscopic surgical system to which the present technology is applied.

In this example, the frame rate of the captured image is greater than or equal to 120 fps. As a result, compared with a case where the frame rate is 60 fps, the latency can be reduced to about half. In a case where signal processing is performed in pipeline, the effect of latency reduction is greater.

11. Endoscopic Surgical Systems of Other Embodiments

In the following, endoscopic surgical systems will be described of other embodiments.

Example 1

Figure 20:
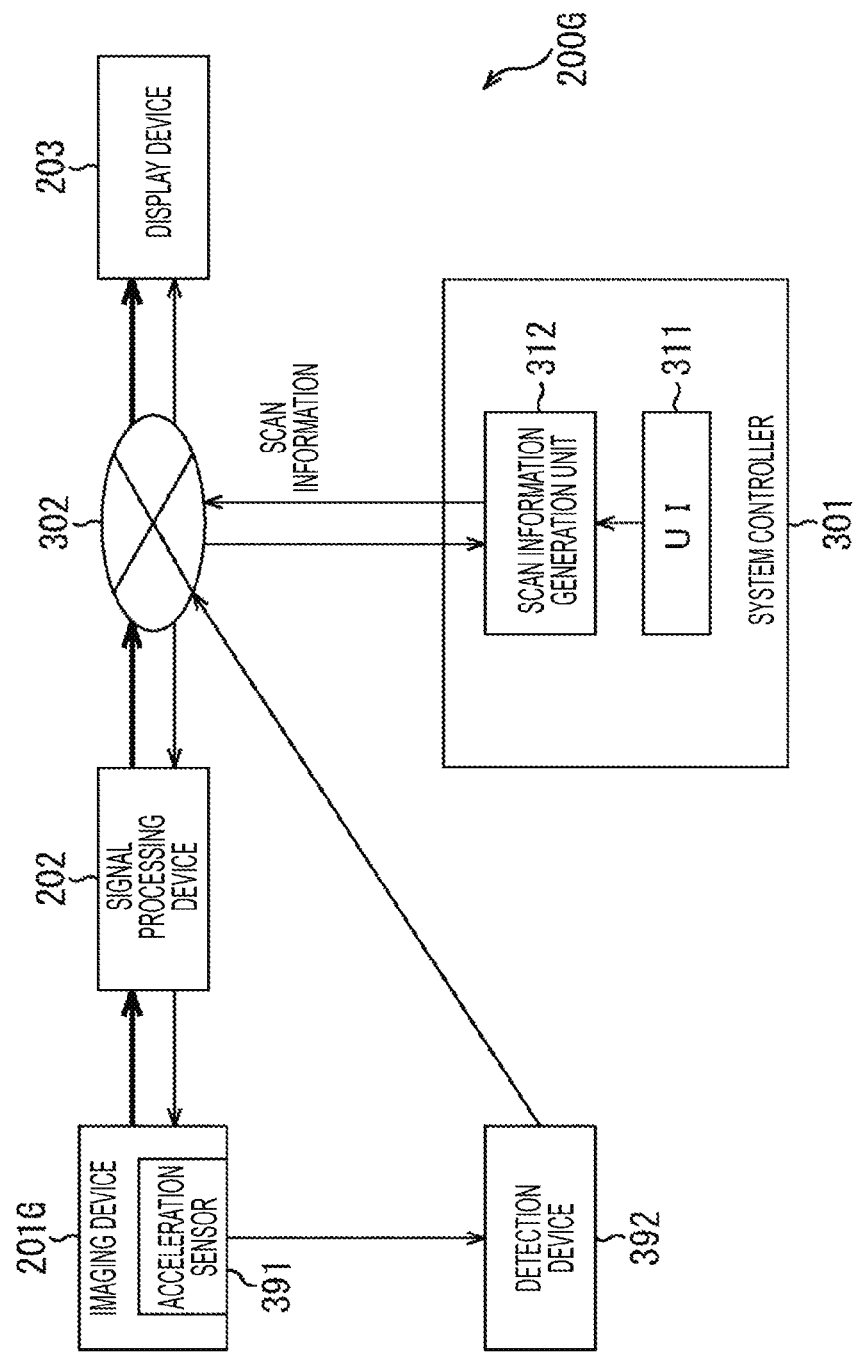
FIG. 20 is a block diagram illustrating yet another functional configuration example of the endoscopic surgical system.

FIG. 20 is a diagram illustrating another functional configuration example of the endoscopic surgical system.

In an endoscopic surgical system 200G of FIG. 20, an imaging device 201G including an acceleration sensor 391 is provided instead of the imaging device 201 of the endoscopic surgical system 200C of FIG. 13. Moreover, in the endoscopic surgical system 200G of FIG. 20, a detection device 392 is newly provided. In the example of FIG. 20, the signal processing device 202, the display device 203, the system controller 301, and the detection device 392 are connected to each other via the network 302.

The detection device 392 detects the direction of gravity on the basis of a signal output from the acceleration sensor 391. On the basis of the detection result, the detection device 392 generates top and bottom information indicating a direction of the top and bottom of the imaging device 201G, and supplies the top and bottom information to the scan information generation unit 312 via the network 302.

The scan information generation unit 312 of FIG. 20 generates scan information on the basis of the top and bottom information from the detection device 392.

As described above, according to the endoscopic surgical system 200G of FIG. 20, respective scan orders for imaging, signal processing, and display can be determined depending on the direction of the top and bottom of the imaging device 201G.

Example 2

Figure 21:
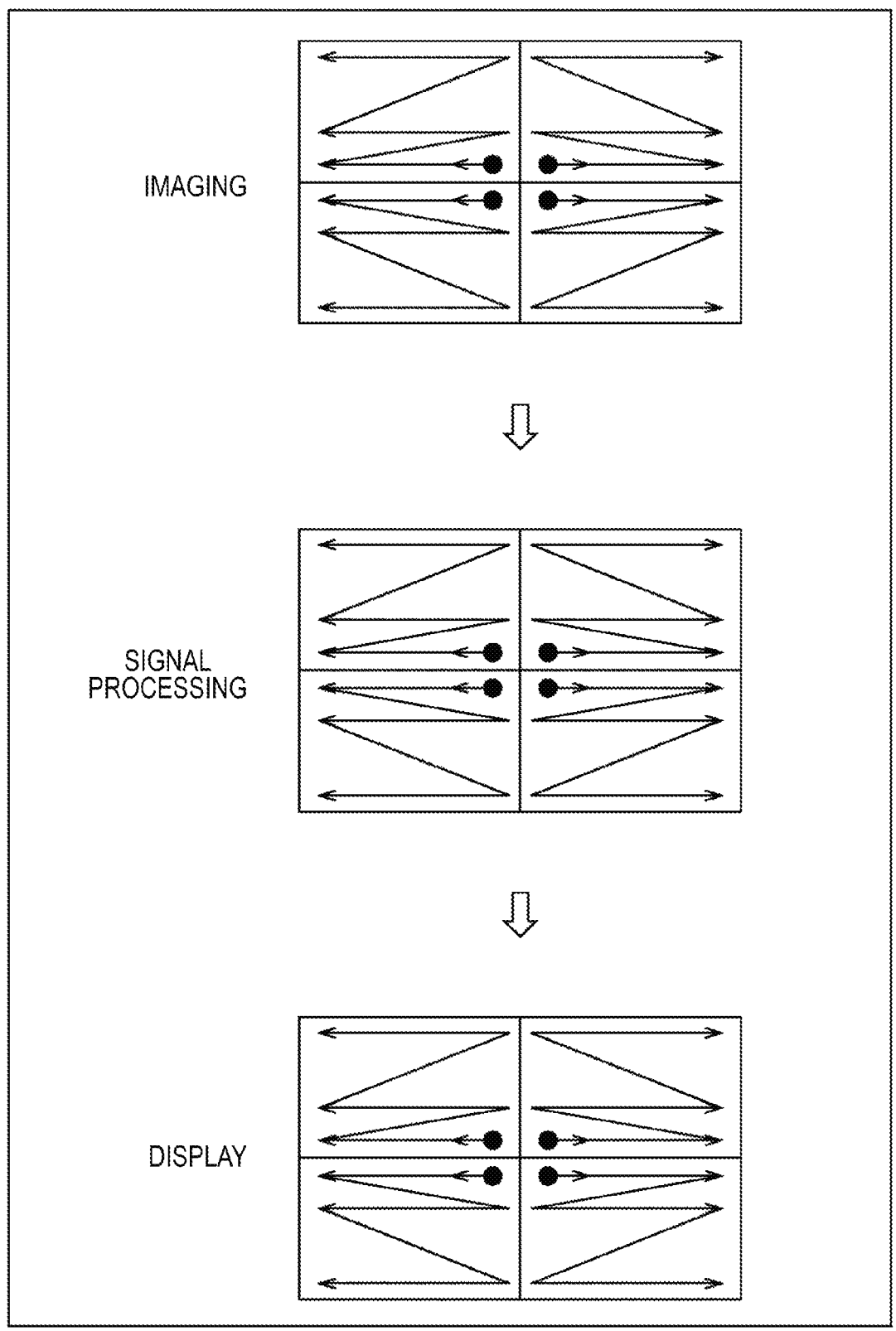
FIG. 21 is a diagram for explaining a scan method that does not depend on a top and bottom direction.

With an increase in the number of pixels in the image sensor and an improvement in the frame rate of the captured image, scanning may be performed of a plurality of patterns for one image, as illustrated in FIG. 21.

First, as illustrated in the first stage from the top of FIG. 21, the imaging device acquires pixel data by scanning each area obtained by dividing the captured image into four areas, in the dot sequential manner from the center of the captured image toward the four corners, and sequentially transmits the pixel data to the signal processing device.

Specifically, scanning is performed from the lower right to the upper left in the upper left area obtained by dividing the captured image into four areas, and from the lower left to the upper right in the upper right area. Furthermore, scanning is performed from the upper right to the lower left in the lower left area, and from the upper left to the lower right in the lower right area.

Next, as illustrated in the second stage of FIG. 21, the signal processing device performs signal processing by scanning each area obtained by dividing the captured image into four areas, in the dot sequential manner from the center of the captured image toward the four corners, similarly to the imaging device.

Then, as illustrated in the third stage of FIG. 21, the display device performs display by scanning each area obtained by dividing the captured image into four areas, in the dot sequential manner from the center of the captured image toward the four corners, similarly to the imaging device.

With such a scan method, even in a case where inversion is specified of the top and bottom direction of the captured image to be displayed on the display device, the display device only needs to display the captured image in the order scanned by the imaging device, and can perform scanning for display without waiting for completion of storage of one image in the memory.

Example 3

In the above description, the configuration has been described in which the scan order in the vertical direction of the captured image is determined by the scan information. Here, the scan order in the vertical direction is a scan order from the upper left to the upper right, from the lower left to the lower right of the captured image in the dot sequential manner, or a scan order from the top to the bottom of the captured image in the line sequential manner or the block sequential manner.

Not limited to the above-described configuration, the scan order in the left-right direction of the captured image may be determined by the scan information. Specifically, scanning may be performed in a scan order from the upper left to the lower left, from the upper right to the lower right of the captured image in the dot sequential manner, or in a scan order from the left to the right of the captured image in the line sequential manner or the block sequential manner.

In this case, for example, the imaging device performs scanning in the scan order from the upper left to the lower left, from the upper right to the lower right of the captured image in the dot sequential manner on the basis of the scan information, as illustrated in FIG. 22A, or, conversely, performs scanning in a scan order from the lower right to the upper right, from the lower left to the upper left of the captured image in the dot sequential manner, as illustrated in FIG. 22B. Furthermore, the display device comes to have, as an inversion display function, a function of rotating by 180 degrees and displaying the captured image, and a function of mirror-inverting in the left-right direction and displaying the captured image.

12. Others

Figure 23:
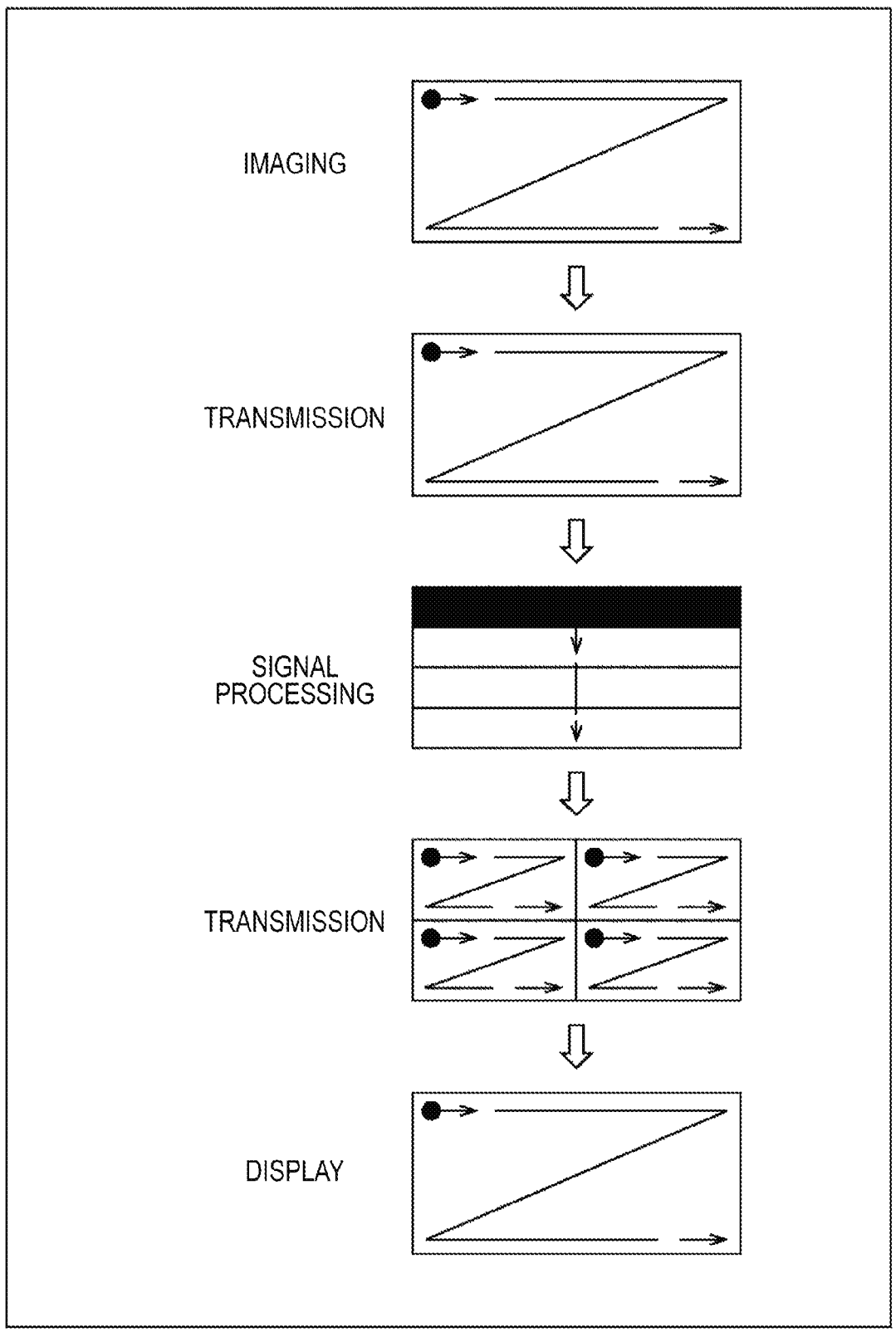

FIG. 23 illustrates an example in which a scan method at the time of data transmission from the signal processing device to the display device does not match a scan method in the display device.

In the example of FIG. 23, latencies of 0.5V occur respectively when a scan method of the signal processing device is converted to the scan method at the time of data transmission to the display device, and when the scan method at the time of data transmission to the display device is converted to the scan method in the display device.

As in the present embodiment described above, the latency can be reduced by matching the scan method at the time of data transmission from the signal processing device to the display device with the scan method in the display device.

Note that, the configurations of the embodiments and modifications described above may be applied alone or in combination.

In the above, the example has been described of the operation room system 10 to which the technology according to the present disclosure can be applied. Note that, here, as an example, the case has been described where the surgical system to which the operation room system 10 is applied is the endoscopic surgical system 23, but the configuration of the operation room system 10 is not limited to such an example. For example, the operation room system 10 may be applied to an inspection flexible endoscopic surgical system or a microscopic surgical system instead of the endoscopic surgical system 23.

Furthermore, the embodiment of the present technology is not limited to the embodiments described above, and various modifications are possible without departing from the scope of the present technology.

Moreover, the present technology can also adopt the following configurations.

(1)

A surgical system including:

a surgical imaging device that generates a surgical image by imaging the inside of a living body;

a signal processing device that performs predetermined signal processing on the surgical image; and a display device that displays the surgical image on which the signal processing is performed, in which the surgical imaging device generates the surgical image on the basis of scan information indicating a scan order of the surgical image.

(2)

The surgical system according to (1), in which the signal processing device performs the signal processing on the surgical image on the basis of the scan information, and the display device displays the surgical image on the basis of the scan information.

(3)

The surgical system according to (1) or (2), further including a scan information generation unit that generates the scan information depending on the top and bottom direction of the surgical image to be displayed on the display device.

(4)

The surgical system according to (3), in which the display device includes: a user interface that accepts specification of the top and bottom direction of the surgical image to be displayed on the display device; and the scan information generation unit, and the scan information generation unit generates the scan information on the basis of the specification of the top and bottom direction of the surgical image accepted by the user interface.

(5)

The surgical system according to (3), in which the signal processing device includes: a user interface that accepts specification of the top and bottom direction of the surgical image to be displayed on the display device; and the scan information generation unit, and the scan information generation unit generates the scan information on the basis of the specification of the top and bottom direction of the surgical image accepted by the user interface.

(6)

The surgical system according to (3), in which the surgical imaging device includes: a user interface that accepts specification of the top and bottom direction of the surgical image to be displayed on the display device; and the scan information generation unit, and the scan information generation unit generates the scan information on the basis of the specification of the top and bottom direction of the surgical image accepted by the user interface.

(7)

The surgical system according to (3), further including a controller that controls each device constituting the surgical system, in which the controller includes: a user interface that accepts specification of the top and bottom direction of the surgical image to be displayed on the display device; and the scan information generation unit, and the scan information generation unit generates the scan information on the basis of the specification of the top and bottom direction of the surgical image accepted by the user interface.

(8)

The surgical system according to any of (3) to (7), further including a plurality of the display devices, in which the user interface accepts specification of the top and bottom direction of the surgical image displayed on each of the plurality of display devices.

(9)

The surgical system according to (1), further including a scan information generation unit that generates the scan information on the basis of a positional relationship among a user, the surgical imaging device, and the display device.

(10)

The surgical system according to (1), in which the surgical imaging device is configured as a camera including a plurality of image sensors, and performs imaging such that scan orders for images on the respective image sensors are identical to each other, on the basis of the scan information.

(11)

The surgical system according to (1), in which the surgical imaging device has a digital zoom function, and generates the surgical image corresponding to a pixel area necessary for zoom display on an image sensor, on the basis of the scan information.

(12)

The surgical system according to (1), further including:

a detection device that generates top and bottom information indicating a direction of the top and bottom of the surgical imaging device on the basis of the direction of gravity detected in the surgical imaging device; and the scan information generation unit that generates the scan information on the basis of the top and bottom information.

(13)

The surgical system according to any of (1) to (12), in which the scan information determines the scan order in the vertical direction of the surgical image.

(14)

The surgical system according to any of (1) to (12), in which the scan information determines the scan order in the left-right direction of the surgical image.

(15)

A surgical imaging device including an imaging unit that generates a surgical image by imaging the inside of a living body, in which the imaging unit generates the surgical image on the basis of scan information indicating a scan order of the surgical image corresponding to the top and bottom direction of the surgical image to be displayed on a display device.

REFERENCE SIGNS LIST

10 Operation room system
23 Endoscopic surgical system
29 Camera head
33 Imaging unit
63 CCU
65 Display device
85 Image processing unit
200, 200A to 200G Endoscopic surgical system
201 Imaging device
202 Signal processing device
203 Display device
211 UI
212 Scan information generation unit
231 UI
232 Scan information generation unit
251 UI
252 Scan information generation unit
301 System controller
311 UI
312 Scan information generation unit
331 Intra-OR Camera
352 Imaging unit
392 Detection device

The invention claimed is:

1. A surgical system, comprising:
a camera configured to generate a surgical image by imaging an inside of a living body, wherein the camera includes a sensor configured to output a signal;
a central processing unit (CPU) configured to perform a specific signal processing on the surgical image;
a display device configured to display the surgical image on which the signal processing is performed;
a first circuitry configured to:
detect a direction of gravity based on the signal output from the sensor of the camera; and
generate, based on the detected direction of gravity, top and bottom information that indicates a direction of a top of the camera and a direction of a bottom of the camera; and
a second circuitry configured to:
generate scan information that indicates a scan order of the surgical image based on the top and the bottom information, wherein
the camera is further configured to generate the surgical image based on the generated scan information, and
the scan information is generated based on a positional relationship between a user, the camera, and the display device.

2. The surgical system according to claim 1, wherein
the CPU) is further configured to perform the signal processing on the surgical image based on the scan information, and
the display device is further configured to display the surgical image based on the scan information.

3. The surgical system according to claim 1, wherein
the second circuitry is further configured to generate the scan information based on a top direction and a bottom direction of the surgical image to be displayed on the display device.

4. The surgical system according to claim 3, wherein
the display device includes:
a user interface configured to accept specification of the top direction and the bottom direction of the surgical image to be displayed on the display device, and
the second circuitry is further configured to generate the scan information based on the specification of the top direction and the bottom direction of the surgical image accepted by the user interface.

5. The surgical system according to claim 3, wherein
the CPU includes:
a user interface configured to accept specification of the top direction and the bottom direction of the surgical image to be displayed on the display device, and
the second circuitry is further configured to generate the scan information based on the specification of the top direction and the bottom direction of the surgical image accepted by the user interface.

6. The surgical system according to claim 3, wherein
the camera includes:
a user interface configured to accept specification of the top direction and the bottom direction of the surgical image to be displayed on the display device, and
the second circuitry is further configured to generate the scan information based on the specification of the top direction and the bottom direction of the surgical image accepted by the user interface.

7. The surgical system according to claim 3, further comprising
a controller configured to control each device constituting the surgical system, wherein
the controller includes:
a user interface configured to accept specification of the top direction and the bottom direction of the surgical image to be displayed on the display device, and
the second circuitry is further configured to generate the scan information based on the specification of the top direction and the bottom direction of the surgical image accepted by the user interface.

8. The surgical system according to claim 7, further comprising
a plurality of display devices, wherein
the user interface is further configured to accept specification of the top direction and the bottom direction of the surgical image displayed on each display device of the plurality of display devices.

9. The surgical system according to claim 1, wherein
the camera includes a plurality of image sensors, and
the camera is further configured to perform imaging such that a plurality of scan orders for a plurality of images on a respective image sensor of the plurality of image sensors are identical to each other, based on the scan information.

10. The surgical system according to claim 1, wherein
the camera includes an image sensor,
the camera has a digital zoom function, and
the camera is further configured to generate the surgical image corresponding to a pixel area necessary for zoom display on the image sensor, based on the scan information.

11. The surgical system according to claim 1, wherein the scan information determines the scan order in a vertical direction of the surgical image.

12. The surgical system according to claim 1, wherein the scan information determines the scan order in a left-right direction of the surgical image.

13. A surgical device, comprising:
a camera configured to generate a surgical image by imaging an inside of a living body, wherein
the camera includes a sensor configured to output a signal,
top and bottom information of the surgical image is generated based on direction of gravity,
the top and bottom information indicates a direction of a top of the camera and a direction of a bottom of the camera,
the direction of gravity, detected by a first circuitry, is based on the signal output from the sensor of the camera,
the generated surgical image is based on scan information indicating a scan order of the surgical image based on the top and the bottom information of the surgical image to be displayed on a display device,
the scan information is generated by a second circuitry, and
the scan information is generated based on a positional relationship between a user, the camera, and the display device.

* * * * *